(12) United States Patent
Sessler et al.

(10) Patent No.: US 8,802,074 B2
(45) Date of Patent: Aug. 12, 2014

(54) POLYMERS FUNCTIONALIZED WITH ION-SPECIFIC RECOGNITION ELEMENTS

(75) Inventors: Jonathan L. Sessler, Austin, TX (US); Christopher W. Bielawski, Austin, TX (US); Abdullah Aydogan, Austin, TX (US); Daniel J. Coady, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 302 days.

(21) Appl. No.: 12/623,943

(22) Filed: Nov. 23, 2009

(65) Prior Publication Data

US 2010/0129308 A1    May 27, 2010

Related U.S. Application Data

(60) Provisional application No. 61/118,170, filed on Nov. 26, 2008.

(51) Int. Cl.
| | |
|---|---|
| A61K 31/74 | (2006.01) |
| B01J 20/26 | (2006.01) |
| B01J 20/32 | (2006.01) |
| B01D 15/00 | (2006.01) |
| B01J 45/00 | (2006.01) |

(52) U.S. Cl.
CPC ............... *A61K 31/74* (2013.01); *B01J 20/265* (2013.01); *B01J 20/26* (2013.01); *B01J 20/261* (2013.01); *B01J 20/262* (2013.01); *B01J 20/3255* (2013.01); *B01J 20/3212* (2013.01); *B01J 20/321* (2013.01); *B01D 15/00* (2013.01); *B01J 45/00* (2013.01)
USPC .................... 424/78.1; 424/78.12; 424/78.14; 424/78.16; 424/78.08

(58) Field of Classification Search
None
See application file for complete search history.

(56) References Cited

U.S. PATENT DOCUMENTS

| | | | |
|---|---|---|---|
| 4,438,251 A * | 3/1984 | Herweh | 528/73 |
| 4,478,983 A * | 10/1984 | Parker | 525/332.2 |
| 5,159,065 A | 10/1992 | Sessler et al. | |
| 5,162,509 A | 11/1992 | Sessler et al. | |
| 5,252,720 A | 10/1993 | Sessler et al. | |
| 5,292,414 A | 3/1994 | Sessler et al. | |
| 5,369,101 A | 11/1994 | Sessler et al. | |
| 5,410,045 A | 4/1995 | Sessler et al. | |
| 5,457,195 A | 10/1995 | Sessler et al. | |
| 5,530,123 A | 6/1996 | Sessler et al. | |
| 5,543,514 A | 8/1996 | Sessler et al. | |
| 5,559,207 A | 9/1996 | Sessler et al. | |
| 5,565,552 A | 10/1996 | Magda et al. | |
| 5,569,759 A | 10/1996 | Sessler et al. | |
| 5,587,371 A | 12/1996 | Sessler et al. | |
| 5,599,928 A | 2/1997 | Hemmi et al. | |
| 5,672,490 A | 9/1997 | Sessler et al. | |
| 5,756,724 A | 5/1998 | Vogel et al. | |
| 5,808,059 A | 9/1998 | Sessler et al. | |
| 6,214,566 B1 * | 4/2001 | Asa et al. | 435/7.1 |
| 6,262,257 B1 | 7/2001 | Gale et al. | |
| 6,602,702 B1 | 8/2003 | McDevitt et al. | |
| 6,680,206 B1 | 1/2004 | McDevitt et al. | |
| 6,984,734 B2 | 1/2006 | Sessler et al. | |
| 7,041,819 B2 | 5/2006 | Sessler et al. | |
| 7,122,572 B2 | 10/2006 | Gale et al. | |
| 7,335,795 B2 | 2/2008 | Chang et al. | |
| 2002/0115566 A1 * | 8/2002 | Sessler et al. | 504/218 |
| 2004/0152826 A1 | 8/2004 | Therien et al. | |
| 2005/0137180 A1 | 6/2005 | Robinson et al. | |

FOREIGN PATENT DOCUMENTS

| | | |
|---|---|---|
| EP | 0233701 | 8/1987 |
| WO | 89/08092 | 9/1989 |
| WO | 93/13150 | 7/1993 |
| WO | 97/37995 | 10/1997 |
| WO | 03/018548 | 3/2003 |
| WO | 2009/006075 | 1/2009 |

OTHER PUBLICATIONS http://en.wikipedia.org/wiki/Diabetes#Diagnosis.*
Abdullah et al., Poly(methyl methacrylate)s with Pendant Calixpyrroles: Polymeric Extractants for halide anion salts; The Royal Society of Chemistry, pp. 1455-1457, 2008.
Abdullah et al., Poly(methyl methacrylate)s with Pendant Calixpyrroles and Crown Ethers: Polymeric Extractants for Potassium Halides, pp. 9648-9652; 2008.
Akhlaghinia, B., A New and Convenient Method of Generating Alkyl Isocyanates from Alcohols, Thiols and Trimethylsilyl Ethers Using Triphenylphosphine/2,3-Dichloro-5,6-dicyanobenzoquinone/$Bu_4NOCN$, Synthesis, 2005, pp. 1955-1958.
Allen, W., et al., "Binding of Neutral Substrates by Calix[4]pyrroles," J. Am. Chem. Soc., vol. 118, No. 49, American Chemical Society, Sep. 1996, pp. 12471-12472.
Andreetti, G., "Crystal and Molecular Structure of Cyclo{quarter[(5-t-butyl-2-hydroxy-1,3-phenylene)methylene]} Toluene (1:1) Clathrate," J.C.S. Chem. Comm., The Royal Society of Chemistry, 1979, pp. 1005-1007.

(Continued)

*Primary Examiner* — James Rogers
(74) *Attorney, Agent, or Firm* — Meunier Carlin & Curfman, LLC

(57) ABSTRACT

Polymeric compounds containing polymer backbones functionalized with ion-specific recognition elements and methods for the use of these compounds are described herein. The polymeric compounds may contain multiple types of ion-specific recognition elements depending on a specific application. The polymeric compounds can be used to remove ionic species from a solution, for example, in separations applications in which a single or multiple types of ionic species are desired to be removed from the solution.

23 Claims, 6 Drawing Sheets

(56) References Cited

OTHER PUBLICATIONS

Anzenbacher, P., et al., "Calix[4]pyrroles Containing Deep Cavities and Fixed Walls. Synthesis, Structural Studies, and Anion Binding Properties of the Isomeric Products Derived from the Condensation of p-Hydroxyacetophenone and Pyrrole," *J. Am. Chem. Soc.*, vol. 121, American Chemical Society, Nov. 13, 1999, pp. 11020-11021.

Anzenbacher, P., et al., "Fluorinated Calix[4]pyrrole and Dipyrrolylquinoxaline: Neutral Anion Receptors with Augmented Affinities and Enhanced Selectives," *J. Am. Chem. Soc.*, vol. 122, American Chemical Society, Oct. 7, 2000, pp. 10268-10272.

Anzenbacher, P., et al., "Second Generation Calixpyrrole Anion Sensors," *J. Am. Chem. Soc.*, vol. 122, American Chemical Society, Sep. 8, 2000, pp. 9350-9351.

Aoyama, Y., et al., "Multi-Point Interaction of Phosphates with Protonated Pyridylporphyrin Discrimination of Monoalkyl and Dialkyl Phosphates," *Chemistry Letters*, The Chemical Society of Japan, 1991, pp. 1241-1244.

Arumugam, N., et al., "Convenient Route to Super-Expanded Calixpyrroles: Synthesis of Calix[n]furano[m]pyrroles (n = 3, 4, 6, 8 and m = 2, 4)," *Organic Letters*, vol. 2, No. 20, American Chemical Society, Sep. 1, 2000, pp. 3115-3117.

Asfari, Z., et al., "Quick Synthesis of the First Double Porphyrin Double Calix[4]arene," *Tetrahedron Letters*, vol. 34, No. 4, Elsevier Science Ltd., 1993, pp. 627-628.

Baeyer, A., "Ueber ein Condensationsproduct von Pyrrol mit Aceton," *Ber. Dtsch. Chem. Ges.*, vol. 19, The Royal Society of Chemistry, 1886, pp. 2184-2185.

Beer, P., et al., "A Neutral Upper to Lower Rim Linked Bis-Calix[4]arene Receptor that Recognises Anionic Guest Species," *Tetrahedron Letters*, vol. 36, No. 5, Elsevier Science Ltd., Jan. 1995, pp. 767-770.

Beer, P., et al., "Anion Recognition by Novel Ruthenium(II) Bipyridyl Calix[4]arene Receptor Molecules," *J. Chem. Soc.*, Chem. Commun., The Royal Society of Chemistry, 1994, pp. 1269-1271.

Beer, P., et al., "Anion Recognition by Redox-Responsive Ditopic Bis-Cobaltocenium Receptor Molecules Including a Novel Calix[4]arene Derivative That Binds a Dicarboxylate Dianion," *Organometallics*, vol. 14, American Chemical Society, Jul. 1995, pp. 3288-3295.

Beer, P., et al., "Structures of Potassium encapsulated within the 1,3-Alternate Conformation of Calix[4]arenes," *J. Chem. Soc. Dalton Trans.*, The Royal Society of Chemistry, 1994, pp. 3479-3485.

Beer, P., et al., "Synthesis and Co-ordination Chemistry of a Novel Bis (Benzo Crown Ether) Substituted Calix[4]arene that can Simultaneously Complex Cations and Anions," *J. Chem. Soc. Dalton Trans.*, The Royal Society of Chemistry, Oct. 1995, pp. 3117-3123.

Beer, P., et al., "Synthesis and X-Ray Crystal Structure of a New Redox-active Calix[5]arene Containing a Totally Included Ethanol Molecule," *J. Chem. Soc., Chem. Commun.*, 1995, p. 1851.

Böhmer, V., "Calixarenes, Macrocycles with (Almost) Unlimited Possibilities," *Angew Chem. Intl. Ed. Engl.*, vol. 34, VCH Verlagsgesellschaft, Jul. 1995, pp. 713-745.

Bonar-Law, R., "Porphyrin Synthesis in Surfactant Solution: Multicomponent Assembly in Micelles," *J. Org. Chem.*, vol. 61, American Chemical Society, Jan. 1996, pp. 3623-3634.

Bröring, M., "A Facile and Efficient Method for the Preparation of New meso-Arylbisdipyrrins," *Synthesis*, vol. 9, 2000, pp. 1291-1294.

Brown, W., et al., "The Condensation of Cyclohexanone with Furan and Pyrrole," *Canadian J. of Chem.*, vol. 49, N R C Research Press, 1971, pp. 4017-4022.

Cafeo, G., et al., "From Large Furan-Based Calixarenes to Calixpyrroles and Calix[n]furan[m]pyrroles: Syntheses and Structures," *Angew. Chem. Int. Ed.*, vol. 39, No. 8, Wiley-VCH Verlag, 2000, pp. 1496-1498.

Cafeo, G., et al., "The complexation of halide ions by a calix[6]pyrrole," *Chem. Commun.*, The Royal Society of Chemistry, 2000, pp. 1207-1208.

Callaway, W., et al., "Schiff-base porphyrin and expanded porphyrin analogues," *J Porphy Pthalocyan*, vol. 8, 2004, pp. 1-25.

Chelintzev, et al., "Simple condensation of pyrrole with cyclohexanone and other cyclic ketones in mixed condensation with acetone and cyclohexanone, and conclusions in respect to the ability of different ketones to condense with pyrrole," *J. Russ. Phys. Chem. Soc.*, Chemical Abstracts only, vol. 48, American Chemical Society, 1916, pp. 1418-1419.

Chelintzev, et al., "Simple condensation of pyrrole with methylethyl ketone and methylhexyl ketone, mixed condensation with acetone and methylethyl ketone, and relation of these reactions to the determination of the formulas of chlorophyll and hemin," *J. Russian Physical Chem. Soc.*, vol. 48, American Chemical Society, 1916, pp. 1197-1209.

Chelintzev, et al., "Process of condensation of pyrrole and acetone. Constitution of the resulting products," *J. Russian Physical Chem. Soc.*, Chemical Abstracts only, vol. 48, American Chemical Society, 1916, pp. 452-454.

Chen, Z., et al., "Synthesis and electrochemical polymerization of calix[4]arenes containing N-substituted pyrrole moieties," *J. Electroanalytical Chem.*, vol. 393, Elsevier Science Ltd., Aug. 1995, pp. 113-117.

Clark, D., et al., "Actinide Carbonate Complexes and Their Importance in Actinide Environmental Chemistry," *Chem Rev*, vol. 95, 1995, pp. 25-48.

Collins, G., et al., "Microfabricated Capillary Electrophoresis Sensor for Uranium (VI)," *Anal Chim Acta*, vol. 436, 2001, pp. 181-189.

Crescenzi, R., et al., "The $N_2O_2$ porphyrinogen skeleton: Access to a novel class of coordinatively unsaturated transition metal ions," *Inorganic Chem.*, vol. 35, American Chemical Society, Apr. 1996, pp. 2413-2414.

Davis, J., "Sapphyrins: Aggregation and Anion Binding Behavior in Polar, Protic Media," Ph.D. Dissertation, The University of Texas at Austin, 2001, 182 pages.

De Angelis, S., et al., "A $Li_2Ti_2$-substituted acetylene formed from ethylene by reaction with (meso-octaethyl porphyrinogen)titanium," *Angewante Chemie*, International Edition, vol. 34 (English), V C H Verlagsgesellschaft, Jun. 1995, pp. 1092-1094.

De Angelis, S., et al., "Organometallic chemistry of a titanium (IV) meso-octaethylporphyrinogen complex: Carrier properties of polar organometallics and their behavior in insertion reactions," *Organometallics*, vol. 14, American Chemical Society, Oct. 1995, pp. 4505-4512.

De Angelis, S., et al., "Oxidation of metal-*meso*-octaethylporphyrinogen complexes leading to novel oxidized forms of porphyrinogen other than porphyrins. 1. The redox chemistry of nickel (II)- and copper (II)-*meso*-octaethylporphyrinogen complexes occurring with the formation and cleavage of a cyclopropane unit," *J. Am. Chem. Soc.*, vol. 116, American Chemical Society, 1994, pp. 5691-5701.

De Angelis, S., et al., "Oxidation of metal-*meso*-octaethylporphyrinogen complexes leading to novel oxidized forms of porphyrinogen other than porphyrins. 2. The redox chemistry of iron (II)- and cobalt (II)-*meso*-octaethylporphyrinogen complexes occurring with the formation and cleavage of two cyclopropane units," *J. Am. Chem. Soc.*, vol. 116, American Chemical Society, 1994, pp. 5702-5713.

De Angelis, S., et al., "Solvent-dependent Forms of Lithiated 5,5,10,10,15,15,20,20-Octaethylporphyrinogen in Solution and in the Solid State and Reaction with Tetrahydrofuran," *J. Chem. Soc.*, Dalton Trans., The Royal Society of Chemistry, 1994, pp. 2467-2469.

Dennstedt, et al., "Ueber die Einwirkung des Acetons auf das Pyrrol," *Ber. Dtsch. Chem. Ges.*, vol. 20, The Royal Society of Chemistry, 1887, pp. 850-857.

Dietrich, B., et al., "Macrocyclic Chemistry: aspects of organic and inorganic supramolecular chemistry," VCH Verlagsgesellschaft, New York, 1993, pp. 82 and 160.

Fish, R., et al., "Removal and recovery of toxic metal ions from aqueous waste streams by utilization of polymer pendant Ligands," *Internet*, posted Oct. 10, 1995, 2 pages.

Floriani, C., "The discovery and future prospects of artificial porphyrins: Molecular batteries functioning with the reversible formation and cleavage of cyclopropane units," *Chimia*, vol. 50, Neue Schweizerische Chemische Gesellschaft, Dec. 1996, pp. 608-611.

Floriani, C., "The porphyrinogen-porphyrin relationship: the discovery of artificial porphyrins," *Chem Commun.*, The Royal Society of Chemistry, Jun. 1996, pp. 1257-1263.

(56) References Cited

OTHER PUBLICATIONS

Floriani, C., "Transition metal complexes as bifunctional carriers of polar organometallics: Their application to large molecule modifications and to hydrocarbon activation," *Pure and Applied Chem.*, vol. 68, Blackwell Science Ltd., Jan. 1996, (IUPAC), pp. 1-8.
Freemantle, M., "Calixarene Family Embraces New Cousins," *Chemical & Engineering News*, vol. 76, No. 7, Feb. 16, 1998, 2 pages.
Fujimoto, K., et al., "Synthesis and Crystallographic Studies of Calix[4]arene with a 1,3-Alternate Conformation," *J. Chem. Soc.*, Perkin Trans. 2, Royal Society of Chemistry, 1992, pp. 643-648.
Furusho, Y., et al., "Molecular Design and Functions of Novel Porphyrinogens," *67th Annual Meeting of the Chemical Society of Japan*, Tokyo, Abstract 3D238 (in Japanese with English translation), *The Chemical Society of Japan*, 1994, 2 pages.
Furusho, Y., et al., "Guest responsive structural changes of porphyrinogen inclusion crystals: a long-range cooperative effect on guest inclusion," *Chemical Communications*, p. vii and Cover page, No. 22, The Royal Society of Chemistry, Nov. 21, 1997, pp. 2205-2206.
Gale, P., et al., "A colourimetric calix[4]pyrrole-4-nitrophenolate based anion sensor," *Chem. Commun.*, The Royal Society of Chemistry, 1999, pp. 1851-1852.
Gale, P., et al., "Calixpyrroles," *Chem. Commun.* The Royal Society of Chemistry, 1998, pp. 1-8.
Gale, P., et al., "Calix[4]pyrroles: C-rim substitution and tenability of anion binding strength," *Chem. Commun.*, The Royal Society of Chemistry, 1997, pp. 665-666.
Gale, P., et al., "Calix[4]pyrroles: Old Yet New Anion Binding Agents," *J. Am. Chem. Soc.*, vol. 118, American Chemical Society, 1996, pp. 5140-5141.
Gale, P., et al., "First Synthesis of an Expanded Calixpyrrole," *Tetrahedron Letters*, vol. 38, No. 49, Elsevier Sciences Ltd., 1997, pp. 8443-8444.
Gale, P., et al., "Synthesis of a New Cylindrical Calix[4]arene-Calix[4]pyrrole Pseudo Dimer," *Tetrahedron Letters*, vol. 37, No. 44, Elsevier Sciences Ltd., Sep. 1996, pp. 7881-7884.
Ghidini, E., et al., "Complexation of Alkai Metal Cations by Conformationally Rigid, Stereoisomeric Calix[4]arene Crown Ethers: A Quantitative Evaluation of Preorganization," *J. Am. Chem. Soc.*, vol. 112, American Chemical Society, 1990, pp. 6979-6985.
Golder, A., et al., "5,10,15,20-*meso*-tetrakis3,5-di-t-butyl-4-quinomethide)porphyrinogen: a highly puckered tetrapyrrolic macrocycle from the facile aerial oxidation of a phenolic porphyrin," *J. Chem. Soc., Chemical Communications*, The Royal Society of Chemistry, 1989, pp. 1751-1753.
Goodey, A., et al., "Development of Multianalyte Sensor Arrays Composed of Chemically Derivatized Polymeric Microspheres Localized in Micromachined Cavities," *J Am. Chem. Soc.*, vol. 123, 2001, pp. 2559-2570.
Goodey, A., et al., "Multishell Microspheres with Integrated Chromatographic and Detection Layers for Use in Array Sensors," *J Am Chem Soc*, vol. 125, 2003, pp. 2870-2871.
Gutsche, C., et al., "Calixarenes. 4. The Synthesis, Characterization, and Properties of the Calixarenes from p-tert-Butylphenol," *J. Am. Chem. Soc.*, vol. 103, No. 13, American Chemical Society, 1981, pp. 3782-3792.
Gutsche, C. "Calixarenes," *Monographs in Supramolecular Chemistry*, ix-xii, Title Page and Table of Contents only, Royal Society of Chemistry, 1989, 4 pages.
Isoz, S., et al., "Niobium—carbon functionalities supported by *meso*-octaethylporphyrinogen and derived macrocycles," *Organometallics*, vol. 15, American Chemical Society, Jan. 1996, pp. 337-344.
Iverson, B., et al., "Molecular Recognition of Anionic Species by Silica Gel Bound Sapphyrin," *J. Am. Chem. Soc.*, vol. 116, American Chemical Society, 1994, pp. 2663-2664.
Jacoby, D., et al., "Bifunctional carriers of organometallic functionalities: alkali-metal-zirconium-hydrido, -alkyl, and -allyl derivatives of *meso*-octaethylporphyrinogen and their reaction with isocyanides," *Organometallics*, vol. 14, American Chemical Society, Oct. 1995, pp. 4816-4824.

Jacoby, D., et al., Electrophilic activation of aliphatic C—H bonds mediated by zirconium hydride entities and applied to the functionalization of the porphyrinogen periphery, *J. Amer. Chem. Soc.*, vol. 117, American Chemical Society, Mar. 1995, pp. 2805-2816.
Jacoby, D., et al., "Macrocyclic modification using organometallic methodologies. Regiochemically controlled mono- and bis-homologation reactions of porphyrinogen with carbon monoxide assisted by early transition metals," *J. Amer. Chem. Soc.*, vol. 117, American Chemical Society, Mar. 1995, pp. 2793-2804.
Jacoby, D., et al., "*meso*-Octamethylporphyrinogen metal complexes: an entry to high valent unsaturated metal centres," *J. Chem. Soc., Chemical Communications*, The Royal Society of Chemistry, 1991, pp. 220-222.
Jacoby, D., et al., "The $\pi$ and $\sigma$ Bonding Modes of *meso*-Octaethylporphyrinogen to Transition Metals: the X-ray Structure of *meso*-Octaethylporphyrinogen-Zirconium (IV) Complex and of the Parent *meso*-Octaethylporphyrinogen Ligand," *J. Chem. Soc., Chemical Communications*, The Royal Society of Chemistry, 1991, pp. 790-792.
Jacoby, D., et al., "Zirconium *meso*-Octaethylporphyrinogen as a carrier for sodium hydride in toluene: Zirconium—sodium bimetallic hydride and alkyls," *J. Am. Chem. Soc.*, vol. 115, American Chemical Society, 1993, pp. 3595-3602.
Jang, Y-S, et al., "Synthesis of calix[n]pyrroles and calix[n]thieno[n]pyrroles (n = 2, 3, 4) by '3+1' approach," *Tetrahedron Letters*, vol. 41, Elsevier Sciences Ltd., 2000, pp. 2919-2923.
Jones, R., et al., "Mechanism of heterocyclic ring expansions. Part III. Reaction of pyrroles with dichlorocarbene," *J. Chem. Soc.*, The Royal Society of Chemistry, 1969, pp. 2249-2251.
Jones, R., et al., "Mechanism of heterocyclic ring expansions. Part IV. Reaction of an imidazole,,pyrazole and 1,2,4-triazole with dichlorocarbene," *J. Chem. Soc.*, The Royal Society of Chemistry, 1969, pp. 2251-2255.
Jones, R., et al., "Mechanism of heterocyclic ring expansions. Part V. Base catalyzed rearrangement of 2-dichloromethyl-2,5-dimethyl-2*H*-pyrrole and related compounds," *J. Chem. Soc.*, The Royal Society of Chemistry, 1969, pp. 2255-2259.
Jubb, J., et al., "Preparation and reactivity of the first yttrium porphyrinogen complex," *J. Chem. Soc., Chemical Communications*, The Royal Society of Chemistry, 1994, pp. 2641-2642.
Jubb, J., et al., "Redox chemistry of *meso*-Octaethylporphyrinogen: Formation and opening of a cyclopropane ring," *J. Am. Chem. Soc.*, vol. 114, American Chemical Society, 1992, pp. 6571-6573.
Jubb, J., et al., "Lithium-Transition Metal Complexes Derived from *meso*-Octaethylporphyrinogen Which Display $\alpha$- and $\pi$- Bonding Modes," *Inorganic Chem.*, vol. 31, American Chemical Society, 1992, pp. 1306-1308.
Kamlet, M., et al., "Linear Solvation Energy Relationships. 23. A Comprehensive Collection of the Solvatochromic Parameters, $\pi^*$, $\alpha$, and $\beta$, and Some Methods for Simplifying the Generalized Solvatochromic Equation," *J. Org. Chem.*, vol. 48, American Chemical Society, 1983, pp. 2877-2887.
Kobayashi, N., et al., "A 'calix[4]arened' porphyrin as a new host and an oxygen carrier model," *Inorganica Chimica Acta*, vol. 224, Elsevier Sciences Ltd., 1994, pp. 1-3.
Král, V., et al., "A Non-Ionic Water-Soluble Pentaphyrin Derivative. Synthesis and Cytotoxicity," *Bioorganic & Medicinal Chemistry*, vol. 3, No. 5, 1995, pp. 573-578.
Král, V., et al., "Synthesis and Biolocalization of Water Soluble Sapphyrins," *J Med Chem*, vol. 45, 2002, pp. 1073-1078.
Kubo, Y., et al., "A Uranyl Ion-sensitive Chromoionophore Based on Calix[6]arene," *J Chem Soc Chem Commun*, 1994, pp. 1725-1726.
Kursanov, N., "Cyclehexyl phenyl ether and its isomerization to cyclohexylphenol," *J. Russ. Phys. Chem. Soc.*, Chemical Abstracts only, vol. 48, American Chemical Society, 1916, pp. 1172-1174.
Lee, J., "Cyclo[n]pyrroles and Their Applications," Ph.D. Dissertation, The University of Texas at Austin, May 2006, 155 pages.
Marx, T., et al., "A Porphyrinogen bridged with and a Porphyrin Substituted by 1,8-diethynylanthracene," *Liebigs Ann. Chem.*, V C H Verlagsgesellschaft, 1994, pp. 857-858.

(56) References Cited

OTHER PUBLICATIONS

Marx, T., et al., "Ein Porphyrinogen mit 1,8-Diphenylanthracen-Brücke," *Liebigs Ann. Chem.*, V C H Verlagsgesellschaft, 1993, pp. 1041-1042.

Melfi, P., et al., "Redox Behavior of Cyclo[6]pyrrole in the Formation of a Uranyl Complex," *Inorg Chem*, vol. 46, 2007, pp. 5143-5145.

Miyaji, H., et al., "Anthracene-linked calix[4]pyrroles: fluorescent chemosensors for anions," *Chem. Commun.*, The Royal Society of Chemistry, 1999, pp. 1723-1724.

Miyaji, H., et al., "Naked-Eye Detection of Anions in Dichloromethane: Colorimetric Anion Sensors Based on Calix[4]pyrrole," *Angew. Chem. Int. Ed.*, vol. 39, No. 10, Wiley-VCH Verlag., 2000, pp. 1777-1780.

Morzherin, Y., et al., "Chlorosulfonylated Calix[4]arenes: Precursors for Neutral Anion Receptors with a Selectivity for Hydrogen Sulfate," *J. Org. Chem.*, vol. 58, American Chemical Society, 1993, pp. 7602-7605.

Nagasaki, T., et al., "Calix[4]arene-Capped Tetraphenylporphyrin: Synthetic Approach to a Chiral Capped Porphyrin with Regular $C_4$ Symmetry," *Chem. Letters*, The Chemical Society of Japan, 1994, pp. 989-992.

Nagasaki, T., et al., "Design and synthesis of a $C_4$-symmetrical hard-soft ditopic metal receptor by calixarene-porphyrin coupling," *J. Chem. Soc. Perkin Trans.*, vol. 1, Royal Society of Chemistry, Aug. 1995, pp. 1883-1888.

No, K., et al., "Synthesis and Molecular Structure of Calix[4]arene Butanoate 1,2-Alternate Conformer," *Bull. Korean Chem. Soc.*, vol. 17, Korean Chemical Society, 1996, pp. 447-452.

Pappalardo, S., et al., "Novel 1,2-Bridged Calix[4]crowns in the 1,2-Alternate Conformation," *Tetrahedron Letters*, vol. 37, No. 22, Elsevier Sciences Ltd., May 1996, pp. 3907-3910.

Petkewich, R., "Polymer Pulls Ion Pairs from Water," *Chemical and Engineering News*, vol. 86, No. 43, Oct. 27, 2008, p. 9.

Piarulli, U., et al., "Redox chemistry associated with the compexation of vanadium (V) and tungsten (VI) by meso-Octaethylporphyrinogen: Formation and cleavage of cyclopropane units functioning as shuttles of two electrons," *J. Am. Chem. Soc.*, vol. 118, American Chemical Society, Mar. 1996, pp. 3634-3642.

Piarulli, U., et al., "The Four-electron Oxidation of meso-Octaethylporphyrinogen via a Metal-mediated Dealkylation Process: Formation of [RuL(PhCN)$_2$][H$_2$L=5,15-dihydro-5,5,10,15,15,20-hexaethylporphyrin]," *J. Chem. Soc., Chemical Communication*, Royal Society of Chemistry, 1994, pp. 895-896.

Rees, C., et al., "The mechanism of heterocyclic ring expansions. Part I. The reaction of 2,3-dimethylindole with dichlorocarbene," *J. Chem. Soc.*, Royal Society of Chemistry, 1964, pp. 928-937.

Rees, C., et al., "The mechanism of heterocyclic ring expansions. Part II. The reaction of methylindoles with halogenocarbenes," *J. Chem. Soc.*, Royal Society of Chemistry, 1964, pp. 938-945.

Rexhausen, H., et al., "The Synthesis of a New 22π Electron Macrocycle: Pentaphyrin," *J Chem Soc Chem Commun*, 1983, p. 275.

Roberto, J., et al., "Report of the Basic Energy Sciences Workshop on Basic Research Needs for Advanced Nuclear Energy Systems," Office of Basic Energy Sciences, Jul. 31-Aug. 3, 2006, DOE: Oct. 2006, pp. 123-128.

Rohwer, H., et al., "Interactions of Uranium and Thorium with Arsenazo III in an Aqueous Medium," *Anal Chim Acta*, vol. 341, 1997, pp. 263-268.

Rosa, A., et al., "The σ- and π- bonding modes of a tetraanionic porphyrinogen ligand in zirconium (IV) complexes: a theoretical investigation," *J. Chem. Soc.*, Dalton Transactions, Royal Society of Chemistry, 1993, pp. 3759-3766.

Rothemund, P., et al., "Concerning the structure of acetone-pyrrole," *J. Am. Chem. Soc.*, vol. 77, American Chemical Society, 1955, pp. 3340-3342.

Rudkevich, D., et al., "Bialix[4]arene-Zn-tetraarylporphyrins," *Tetrahedron Letters*, vol. 35, No. 38, Elsevier Sciences Ltd., 1994, pp. 7131-7134.

Sawicki, M., et al., "Discovery of Powerful Uranyl Ligands From Efficient Synthesis and Screening," *Chem Euro J*, vol. 11, 2005, pp. 3689-3697.

Scheerder, J., et al., "Complexation of Halide Anions and Tricarboxylate Anions by Neutral Urea-Derivatized p-tert-Butylcalix[6]arenes," *J. Org. Chem.*, vol. 60, American Chemical Society, Oct. 1995, pp. 6448-6454.

Schmuck, C., et al., "Synthesis of Orthogonally Protected Pyrrole Tricarboxyilic Acide Derivatives: Versatile Building Blocks for Pyrrole-Containing Compounds," *Synthesis*, 2006, pp. 89-96.

Sessler, J.L., et al., "5,15,25-tris-nor-Hexaphyrin: the First Structurally Characterized Linear Hexapyrrin," *J Chem Soc Chem Commun*, 1994, pp. 1289-1290.

Sessler, J.L., et al., "Actinide expanded porphyrin complexes," *Coordination Chemistry Reviews*, vol. 216-217, 2001, pp. 411-434.

Sessler, J.L., et al., "An Efficient, High-Yield Preparation of Substituted 2,2'-Bipyrroles," *Synlett*, 1994, pp. 211-212.

Sessler, J.L., et al., "Anion Binding: Self-Assembly of Polypyrrolic Macrocycles," *Angew. Chem. Int. Ed. Engl.*, vol. 35, V C H Verlagsgesellschaft, Jun. 1996, pp. 2782-2785.

Sessler, J.L., et al., "Anion carriers: New tools for crossing membranes," *ChemTech*, vol. 29, No. 9, American Chemical Society, 1999, pp. 16-24.

Sessler, J.L., et al. "Calix[4]pyrroles: New Solid-Phase HPLC Supports for the Separation of Anions," *Chem. Eur. J*, vol. 4, No. 6, Wiley-VCH Verlag., 1998, pp. 1095-1099.

Sessler, J.L., et al., "Characterization of the interactions between neptunyl and plutonyl cations and expanded porphyrins," *Inorganica Chimica Acta*, vol. 341, 2002, pp. 54-70.

Sessler, J.L., et al., "Direct Synthesis of Expanded Fluorinated Calix[n]pyrroles: Decafluorocalix[5]pyrrole and Hexadecafluorocalix[8]pyrrole," *J. Am. Chem. Soc.*, vol. 122, American Chemical Society, Nov. 15, 2000, pp. 12061-12062.

Sessler, J.L., et al., "Hexaphyrin(1.0.1.0.0.0): A new colorimetric actinide sensor," *Tetrahedron*, vol. 60, 2004, pp. 11089-11097.

Sessler, J.L., et al. "Hexaphyrin(1.0.1.0.0.0): An Expanded Porphyrin Ligand for the Actinide Cations Uranyl ($UO_2^{2+}$) and Neptunyl ($NpO_2^+$)," *Angew Chim Int Ed Engl*, vol. 40, 2001, pp. 591-594.

Sessler, J.L., et al., "Schiff base oligopyrrolic macrocycles as ligands for lanthanides and actinides," *J Alloys and Compounds*, vol. 418, 2006, pp. 171-177.

Sessler, J.L., et al., "Synthesis and characterization of a hexaphyrin(1.0.1.0.0.0) bearing both meso and β-substituents," *J Porphy Pthalocyan*, vol. 11, 2007, pp. 287-293.

Sessler, J.L., et al., "Synthetic Expanded Porphyrin Chemistry," *Angew Chem Int Ed Engl*, vol. 42, 2003, pp. 5134-5175.

Sessler, J.L., et al., "Texaphyrins: New Drugs with Diverse Clinical Applications in Radiation and Photodynamic Therapy," *Biochemical Pharmacology*, vol. 59, 2000, pp. 733-739.

Sessler, J.L., et al., "Texaphyrins: Synthesis and Applications," *Acc Chem Res*, vol. 27, 1994, pp. 43-50.

Sessler, J.L., et al., "The First 'crowned' Expanded Porphyrins," *Tet. Lett*, vol. 36, 1995, pp. 1175-1176.

Sessler, J.L., et al., "Uranium complexes of multidentate N-donor ligands," *Coord Chemistry Reviews*, vol. 250, 2006, pp. 816-843.

Solari, G., et al., "Bifunctional carriers of alkali-metal enolates: the use of zirconium meso-Octaethylporphyrinogen in aldol condensation reactions," *Organometallics*, vol. 16, American Chemical Society, 1997, pp. 508-510.

Solari, E., et al., "Functionalizable 5,5,10,10,15,15,20,20-octaethylporphyrinogen complexes of early transition metals: Synthesis and Crystal Structure of titanium-, vanadium-, and chromium (III) derivatives and a two-electron oxidation of the porphyrinogen skeleton," *J. Chem. Soc.*, Dalton Transactions, Royal Society of Chemistry, 1994, pp. 2015-2017.

Steed, J., et al., "A Water-Soluble "Bear Trap" Exhibiting Strong Anion Complexation Properties," *Angew. Chem. Int. Ed. Engl.*, vol. 33, V C H Verlagsgesellschaft, 1994, pp. 2456-2457.

Suresh, A., et al., "A New Procedure for the Spectrophotometric Determination of Uranium (VI) in the Presence of a Large Excess of Thorium(IV)," *Spectrochim Acta*, vol. 58, 2002, pp. 341-347.

(56) References Cited

OTHER PUBLICATIONS

Turner, B., et al., "Extended Calixpyrroles: *meso*-Substituted Calix[6]pyrroles," *Angew. Chem. Int. Ed.*, vol. 37, No. 18, Wiley-VCH Verlag., 1998, pp. 2475-2478.

Vogel, E., et al., "2,7,12,17-Tetraproplyporphycene-Counterpart of Octaethylporphrin in the Porphycene Series," *Angew. Chem. Int. Ed. Engl.*, vol. 26, No. 9, V C H Verlagsgesellschaft, 1987, pp. 928-931.

Vogel, E., et al., "New Porphycene Ligands: Octaethyl- and Etioporphycene (OEPc and EtioPc- Tetra- and Pentacoordinated Zinc Complexes of OEPc," *Angew. Chem. Intl. Ed. Engl.*, vol. 32, No. 11, V C H Verlagsgesellschaft, 1993, pp. 1600-1604.

von Maltzan, B., "Synthesis of 2,3,7,8,12,13,17,18-octamethylporphyrinogen in almost quantitative yield," *Angewante Chemie, International Edition* (English), V C H Verlagsgesellschaft, 1982, pp. 785-786.

Wallace, D., et al., "Rational Tetraarylporphyrin Synthesis: Tetraarylporphyrins from the MacDonald Route," *J Org Chem*, vol. 58, 1993, pp. 7245-7257.

Wei, W-H, et al., "New Polyethyleneglycol-functionalized Texaphyrins: Synthesis and in vitro Biological Studies," *Dalton Trans*, 2006, pp. 1934-1942.

Wilcox, C., "Design, Synthesis, and Evaluation of an Efficacious Functional Group Dyad. Methods and Limitations in the Use of NMR for Measuring Host-Guest Interactions," *Frontiers in Supramolecular Organic Chemistry and Photochemistry*, edited by Schneider and Dürr, VCH Verlagsgesellschaft, 1991, pp. 123-143.

Woller, E., et al., "A straightforward Synthesis of 3,4-Difluoropyrrole," *J. Org. Chem.*, vol. 63, American Chemical Society, Jul. 17, 1998, pp. 5706-5707.

Xu, W., et al., "Inorganic Inclusion Chemistry: A Novel Anion Inclusion System," *J. Am. Chem. Soc.*, vol. 117, American Chemical Society, Aug. 1995, pp. 8362-8371.

Related U.S. Appl. No. 12/664,524, filed Apr. 1, 2010.

Non-final Office Action, dated Mar. 3, 2011, in connection with related U.S. Appl. No. 12/664,524.

Final Office Action, dated Sep. 1, 2011, in connection with related U.S. Appl. No. 12/664,524.

Non-final Office Action, dated Mar. 13, 2013, in connection with related U.S. Appl. No. 12/664,524.

International Preliminary Report on Patentability and Written Opinion, dated Jan. 5, 2010, in connection with related International Application No. PCT/US2008/067904.

International Search Report, dated Jun. 30, 2009, in connection with related International Application No. PCT/US2008/067904.

Related U.S. Appl. No. 09/939,514, filed Aug. 24, 2001 (Patent No. 7,041,819, issued May 9, 2006).

Non-final Office Action, dated Jul. 15, 2002, in connection with related U.S. Appl. No. 09/939,514.

Final Office Action, dated Mar. 7, 2003, in connection with related U.S. Appl. No. 09/939,514.

Non-final Office Action, dated Apr. 6, 2005, in connection with related U.S. Appl. No. 09/939,514.

International Search Report, dated Mar. 5, 2003, in connection with related International Application No. PCT/US2002/027252.

Related U.S. Application No. 09/838,998, filed Apr. 20, 2001 (Patent No. 7,122,572, issued Oct. 17, 2006).

Non-final Office Action, dated Jul. 15, 2002, in connection with related U.S. Appl. No. 09/838,998.

Final Office Action, dated Mar. 7, 2003, in connection with related U.S. Appl. No. 09/838,998.

Non-final Office Action, dated Mar. 9, 2005, in connection with related U.S. Appl. No. 09/838,998.

Final Office Action, dated Aug. 22, 2005, in connection with related U.S. Appl. No. 09/838,998.

Related U.S. Appl. No. 08/833,379, filed Apr. 4, 1997 (Patent No. 6,262,257, issued Jul. 17, 2001).

International Search Report, dated Aug. 13, 1997, in connection with related International Application No. PCT/US1997/005643.

Indian Application No. 708/MAS/97 to Gale et al., filed Apr. 3, 1997.

* cited by examiner

US 8,802,074 B2

POLYMERS FUNCTIONALIZED WITH ION-SPECIFIC RECOGNITION ELEMENTS

CROSS-REFERENCE TO RELATED APPLICATION

This application claims priority to U.S. Provisional Application No. 61/118,170, filed Nov. 26, 2008, which is incorporated herein by reference in its entirety.

STATEMENT REGARDING FEDERALLY SPONSORED RESEARCH

This invention was made with government support from the National Institutes of Health Grant number GM-58907 and the National Science Foundation Grant number CHE-0645563. The government has certain rights in this invention.

BACKGROUND

The selective separation of alkaline salts and ionic species from aqueous media is useful in various chemical, biological, medical, and industrial applications. For example selective separation techniques can be used in the production of commodity materials (e.g., bromine, potassium, etc.) from high salt sources, such as the Dead Sea and the Great Salt Lake. Selective separation is also used in biological processes such as the regulation of taste and the maintenance of osmotic balance in cells. Such separations also can be useful in medical applications, for example, the removal of ions from blood or reducing the uptake of ions from ingested foods. Removing or controlling ion levels in a subject can be useful in the control or treatment of numerous disease conditions including hyperkalemia and hyperphosphatemia, which are often associated with diabetes or renal failure.

SUMMARY

Polymeric compounds useful in binding ionic species and methods for their use are provided. The polymeric compounds include a polymer backbone that is functionalized with ion-specific recognition elements. The polymer backbone of the polymeric compounds may be functionalized with multiple types of ion-specific recognition elements. The polymeric compounds can be used in methods to remove ionic species from a solution. Additionally, methods to treat or prevent an ion imbalance in a subject including the steps of selecting a subject with or suspected of having an ion imbalance and administering to the subject a polymeric compound as described herein.

The details of one or more examples of the polymeric compounds and methods are set forth in the accompanying drawings, figures, and the description below. Other features, objects, and advantages will be apparent from the description, drawings, and figures, and from the claims.

DETAILED DESCRIPTION

Figure 1:
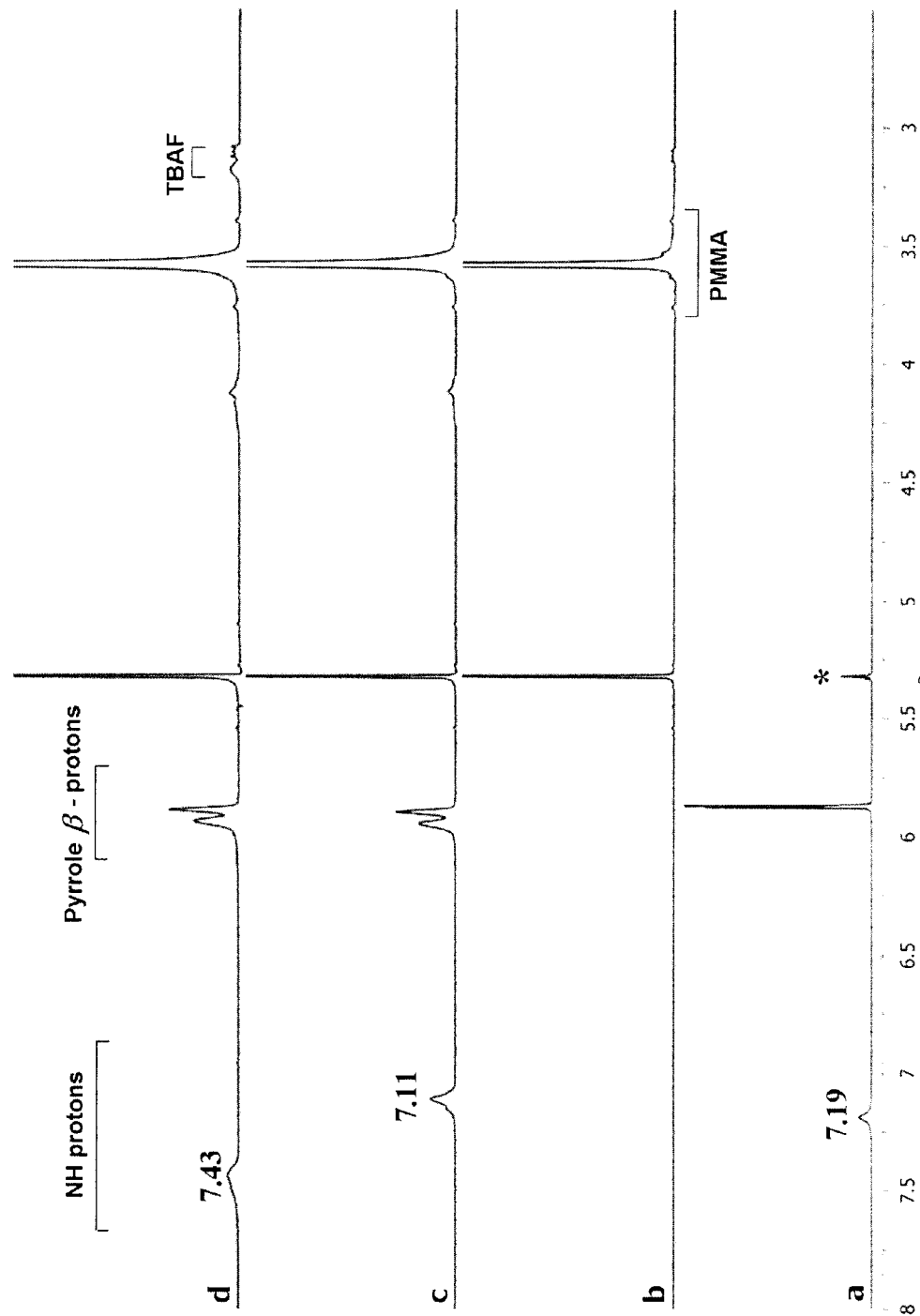
FIG. 1 shows overlaid NMR spectra of $CD_2Cl_2$ solutions of (a) octamethylcalix[4]pyrrole (29 mM) and (b) PMMA (125 mM, based on the repeat unit) after i) adding 0.5 mL of a $D_2O$ solution of TBAF (90 mM), ii) shaking the tube vigorously, and iii) allowing the phases to separate, (c) a calix[4]pyrrole functionalized PMMA homopolymer (effective concentration of the calix[4]pyrrole repeat unit=6.5 mM), (d) a solution of the homopolymer after being subjected to the same treatment applied in the case of (a) and (b) (* indicates residual solvent).

Polymeric compounds including a polymer backbone that is functionalized with ion-specific recognition elements and methods for their use are described herein. The polymer backbone of a polymeric compound as described herein may be functionalized with multiple types of ion-specific recognition elements. The multiple types of ion-specific element may include elements capable of recognizing and/or binding separately or jointly both anionic and/or cationic species. An ion-specific element capable of jointly recognizing anionic and cationic species could recognize separate anionic and cationic molecules or a zwitterionic molecule, i.e., a molecule containing both positively and negatively charges components. Such polymeric compounds can be used to remove ionic species from a solution, for example, in separations applications in which a single or multiple types of ionic species are desired to be removed from a solution (e.g., an aqueous solution).

Ion-specific recognition elements useful with the polymeric compounds described herein include anionic, cationic, and zwitterionic recognition elements. Mixtures of two or more types of ion-specific recognition elements, i.e., anionic, cationic, or zwitterionic, can be used with the polymeric compounds described herein. The term ion-specific recognition element is used herein to indicate a functional element that is capable of binding to or otherwise interacting with (e.g., complexation) an ionic species. Examples of ion-specific recognition elements include calixpyrroles, crown ethers, calixarenes, cryptands, polyaaza, macrocycles, expanded porphyrins, pyrroleamides, indoleamides, substituted ureas, polyamides, and derivatives thereof. Mixtures of ion-specific recognition elements, e.g., a mixture of calixpyrroles and crown ethers, can be used in the same polymeric compound. An example of a calixpyrrole is octamethylcalix[4]pyrrole, which is known to bind halide ions in a 1:1 ratio and has the following structure:

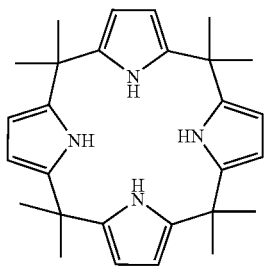 [SMILES: CC1(C)c2ccc([nH]2)C(C)(C)c2ccc([nH]2)C(C)(C)c2ccc([nH]2)C(C)(C)c2ccc1[nH]2]

The methyl groups of the octamethylcalix[4]pyrrole can be replaced with substitutions of various constituents including alkyl, alkenyl, alkynl, heteroalkyl, heteroalkenyl, heteroalkenyl, cycloalkyl, cycloalkenyl, cycloalkynl, cycloheteroalkyl, cycloheteroalkenyl, cycloheteroalkenyl, or aryl groups. Examples of possible substitutions for a methyl group of octamethylcalix[4]pyrrole include:

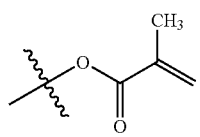 [SMILES: *OC(=O)C(=C)C]

and —$CH_2OH$. An example of a crown ether is a benzo-15-crown-5 ether, which is known to from 2:1 sandwich complexes with potassium cations and has the following structure:

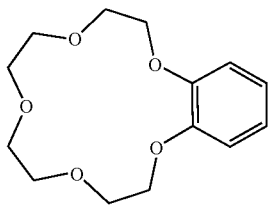 [SMILES: c1ccc2c(c1)OCCOCCOCCOCCO2]

The benzene ring (or other carbon atoms) of the benzo-15-crown-5 ether can be substituted with various constituents including alkyl, alkenyl, alkynl, heteroalkyl, heteroalkenyl, heteroalkenyl, cycloalkyl, cycloalkenyl, cycloalkynl, cycloheteroalkyl, cycloheteroalkenyl, cycloheteroalkenyl, or aryl groups. An example of a substitution group to the benzene ring of a benzo-15-crown-5 ether includes:

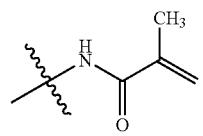 [SMILES: *NC(=O)C(=C)C]

Polymer backbones useful with the polymeric compounds described herein include polymers capable of being functionalized with the ion-specific recognition elements described herein. Examples of polymer backbones suitable for use with the polymeric compounds described herein include homopolymer backbones and co-polymer backbones. The term homopolymer backbone is used herein to indicate a polymer backbone with a single type of repeat unit, e.g., polymethyl methacrylate, polyacryonitrile, polyacrylate, polystyrene, polyester, polyurethane, or polyamide. Polymethyl methacrylate has the following structure:

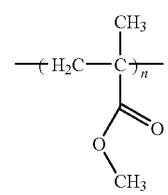

The term co-polymer backbone is used herein to indicate a polymer backbone with multiple (e.g., two or more) types of repeat units, e.g., ABS plastic, SBR, Nitrile rubber, styrene-acrylonitrile, styrene-isoprene-styrene (SIS) and ethylene-vinyl acetate. The multiple types of repeat units can repeat in various patterns, e.g., alternating, periodic, random, block, or with various tacticities, e.g., syndiotactic, isotactic, or random, and be useful with the polymeric compounds as described herein. Various other types of homopolymers and co-polymers useful with the polymeric compounds described herein will be apparent to those of skill in the polymer arts.

Polymeric compounds as described herein include homopolymers and co-polymers. When used in reference to the polymeric compounds described herein, the term homopolymer indicates a polymer that has a uniformly functionalized backbone monomer, e.g., a poly(octamethylcalix[4]pyrrole functionalized methyl methcrylate), which has the following structure:

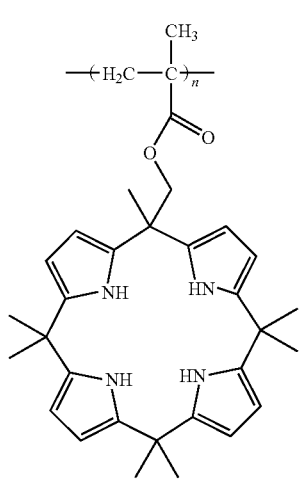

When used in reference to the polymeric compounds described herein, the term co-polymer indicates a polymer that has functionalized backbone monomers that may be spaced apart from each other or multiple, differing functionalized backbone monomers that may be spaced apart from each other. An example of a polymer that has functionalized backbone monomers that may be spaced apart from each other is a polymer with a partially octamethylcalix[4]pyrrole functionalized polymethyl methacrylate backbone, e.g., a compound with the following structure:

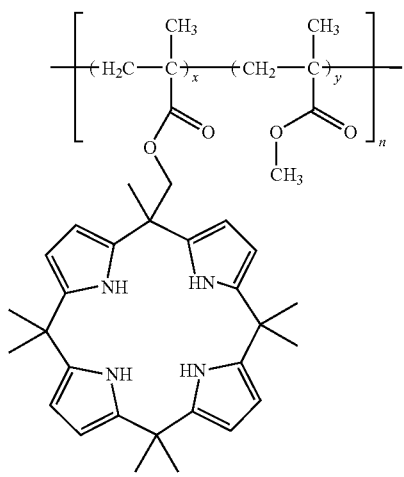

An example of a polymer that has multiple, differing functionalized backbone monomers that may be spaced apart from each other is a multiple (e.g., octamethylcalix[4]pyrrole and benzo-15-crown-5) functionalized polymethyl methacrylate backbone, e.g., a compound with the following structure:

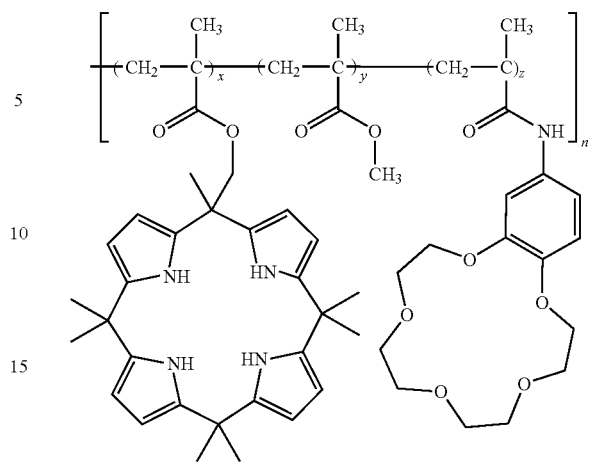

The polymer backbone of the polymeric compounds as described herein can be a homopolymer, as shown by the polymethyl methacrylate backbones used above to illustrate the homopolymer and co-polymer versions of the polymeric compounds as described herein, or, as indicated above, the backbone of the polymeric compounds can be a co-polymer and have a homopolymer or co-polymer type distribution of functional moieties.

The ion-specific recognition elements useful with the polymeric compounds described herein are covalently linked to the polymer backbone. The covalent linkage can be a direct connection to a backbone side chain, e.g., the polymethyl methacrylate side chain, or the linkage can be made through a linker molecule. Linker molecules can themselves be substituted or unsubstituted and include, for example, alkyl, alkenyl, alkynl, heteroalkyl, heteroalkenyl, heteroalkenyl, cycloalkyl, cycloalkenyl, cycloalkynl, cycloheteroalkyl, cycloheteroalkenyl, cycloheteroalkenyl, and aryl groups.

The polymeric compounds described herein can be prepared in a variety of ways known to one skilled in the art of organic synthesis or variations thereon as appreciated by those skilled in the art. The polymeric compounds described herein can be prepared from readily available starting materials. Optimum reaction conditions may vary with the particular reactants or solvents used, but such conditions can be determined by one skilled in the art.

Variations on the polymeric compounds described herein include the addition, subtraction, or movement of the various constituents as described for each compound, as well as modification of the polymer compound's tacticity. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

As used herein, the terms alkyl, alkenyl, and alkynyl include substituted and unsubstituted straight- and branched-chain monovalent substituents. Examples include methyl, ethyl, isobutyl, 3-butynyl, and the like. Heteroalkyl, heteroalkenyl, and heteroalkynyl are similarly defined but may contain O, S, or N heteroatoms or combinations thereof within the backbone. Cyclo versions of alkyl, alkenyl, alkynyl, heteroalkyl, heteroalkenyl, and heteroalkynyl molecules contain a cyclic core, but are similarly defined otherwise and may include various substitutions. The term substituted indicates the main substituent has attached to it one or more additional components, such as, for example, OH, halogen, or one of the substituents listed above.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatograpy (HPLC) or thin layer chromatography.

The methods described herein include a method of using the polymeric compounds described above to remove ionic species from a solution. Ionic species that the polymeric compounds described herein are able to remove include cationic species (such as sodium and potassium and their counter ions), anionic species (such as fluoride, chloride, bromide, and iodine and their counter ions), and zwitterionic species and salts and mixtures thereof. Examples of applications of the methods of using the polymeric compounds described herein may include corrosion prevention (e.g., chloride, carbonate, and sulfate control under conditions of combustion), waste remediation (e.g., sulfate extraction from tank waste), toxin control (e.g., mitigating the effects of overexposure to cyanide or fluoride), and health care (i.e., enhanced phosphate anion or potassium cation removal under conditions of hemodialysis or through ingestion by a subject of the polymeric compounds described herein to help reduce elevated ion levels (e.g., phosphate imbalance disorder). Methods of treating or preventing an ion imbalance in a subject include selecting a subject with or suspected of having an ion imbalance and administering to the subject a polymeric compound as described herein. As used herein treating means providing a therapeutic or prophylactic benefit to the subject, e.g., eradicating, reducing, ameliorating, or preventing an indicated disease or symptom.

The polymeric compounds described herein can be provided in a pharmaceutical composition for administering to a subject. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the compounds described herein in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected substrate without causing significant undesirable biological effects or interacting in a deleterious manner with any of the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). A further consideration in choosing a carrier is the function of the polymeric composition to be carried, e.g., if a polymeric compound as described herein has anionic ion-recognition elements, a carrier that does not contain anions that would be recognized can be chosen.

Compositions containing the polymeric compounds described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration of the compounds described herein include capsules, tablets, pills, powders, and granules. In such solid dosage forms, the polymeric compound described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the polymeric compound or compounds in a certain part of the intestinal tract in a delayed manner. Examples of embedding compositions which can be used are polymeric substances and waxes. The polymeric compounds can also be in micro-encapsulated form, if appropriate, with one or more of the above-mentioned excipients.

Liquid dosage forms for oral administration of the polymeric compounds described herein include pharmaceutically acceptable emulsions, solutions, suspensions, syrups, and elixirs. In addition to the polymeric compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include adjuvants, such as wetting, emulsifying, suspending, sweetening, flavoring, or perfuming agents.

Suspensions, in addition to the polymeric compounds, may contain suspending agents, as for example, ethoxylated isostearyl alcohols, polyoxyethylene sorbitol and sorbitan esters, microcrystalline cellulose, aluminum metahydroxide, bentonite, agar agar and tragacanth, or mixtures of these substances, and the like.

The examples below are intended to further illustrate certain aspects of the methods and compounds described herein, and are not intended to limit the scope of the claims.

EXAMPLES

Example 1

Preparation of Calix[4]pyrrole Functionalized PMMA Homopolymer and Co-Polymer

Calix[4]pyrrole Functionalized PMMA Homopolymer

A N-methylmethacrylamide functionalized calix[4]pyrrole monomer was prepared in 82% yield from a hydroxylmethyl calixpyrrole derivative through treatment with methacryloyl chloride under basic conditions. The N-methylmethacrylamide functionalized calix[4]pyrrole monomer proved amenable to polymerization using conventional free radical methods. See G. Odian, *Principles of Polymerization*, 4th Ed., John Wiley and Sons, Inc., 2004, Chapter 3. A homopolymer was prepared by dissolving the N-methylmethacrylamide functionalized calix[4]pyrrole monomer in THF (0.3 M) followed by treatment with 1 mol % of azoisobutyronitrile (AIBN). After stirring at 70° C. for 17 h under an atmosphere of nitrogen, the resulting viscous solution was added dropwise into excess methanol with rapid stirring. This caused precipitation of the homopolymer, which was later isolated via filtration in 66% yield. Using gel permeation chromatography (GPC), the polymer was found to have a number-average molecular weight ($M_n$) of 23,600 Da (relative to PMMA standards) and a polydispersity index (PDI) of 2.3.

Calix[4]pyrrole Functionalized PMMA Co-Polymer

A copolymer of N-methylmethacrylamide functionalized calix[4]pyrrole and methyl methacrylate (MMA) was prepared using the conventional free radical polymerization protocol described above. The reaction produced a 77% yield of the copolymer from a 1:10 mixture of N-methylmethacrylamide functionalized calix[4]pyrrole monomer and MMA. Using GPC, the copolymer was found to possess a $M_n$ of 85,500 Da and a PDI of 2.1. The co-polymer was highly soluble in most common organic solvents, including dichloromethane.

$^1$H NMR spectroscopic analysis ($CD_2Cl_2$) of the co-polymer indicated that there were approximately fourteen methacrylate units per calixpyrrole unit within the co-polymer. For comparison, a sample of PMMA (Mn=40,700; PDI=1.5) was prepared using a procedure analogous to that used to obtain the homopolymer and copolymer. Thermal analysis of the co-polymer revealed a decomposition temperature ($T_d$) at 272° C., which is intermediate between the respective $T_d$s found for the homopolymer (270° C.) and the PMMA homopolymer (276° C.) used for comparison.

These results indicate that the physical properties of co-polymers prepared from MMA and various methacrylate monomers functionalized with ion-specific recognition elements may be tuned through the selection of specific functionalized monomers.

Example 2

Binding Ions Under Interfacial Conditions Using the co-polymer of Example 1

The ability of the co-polymer to bind anions under interfacial conditions was explored. As shown in FIG. 1, addition of a $D_2O$ solution of tetrabutylammonium fluoride (TBAF, 90 mM) to a $CD_2Cl_2$ solution of the co-polymer (effective concentration of the calix[4]pyrrole repeat unit=6.5 mM) resulted in a substantial downfield shift in the pyrrole NH protons (as typically seen upon anion binding). Further, peaks ascribable to the methylene units in the TBA$^+$ counter cation (at δ=3.2 ppm) were seen, indicating that both the anion (F$^-$) and the cation were present in the organic phase. In contrast, no shifts in the NH resonances and no TBA$^+$-ascribable peaks were observed when a 29 mM solution of octamethylcalix[4]pyrrole in $CD_2Cl_2$ was exposed to aqueous solutions of TBAF. Likewise, no evidence of uptake of TBA$^+$ into the organic phase (absence of any discernible peak at δ=3.2 ppm) was seen when analogous experiments were repeated with the MMA homopolymer.

Figure 2:
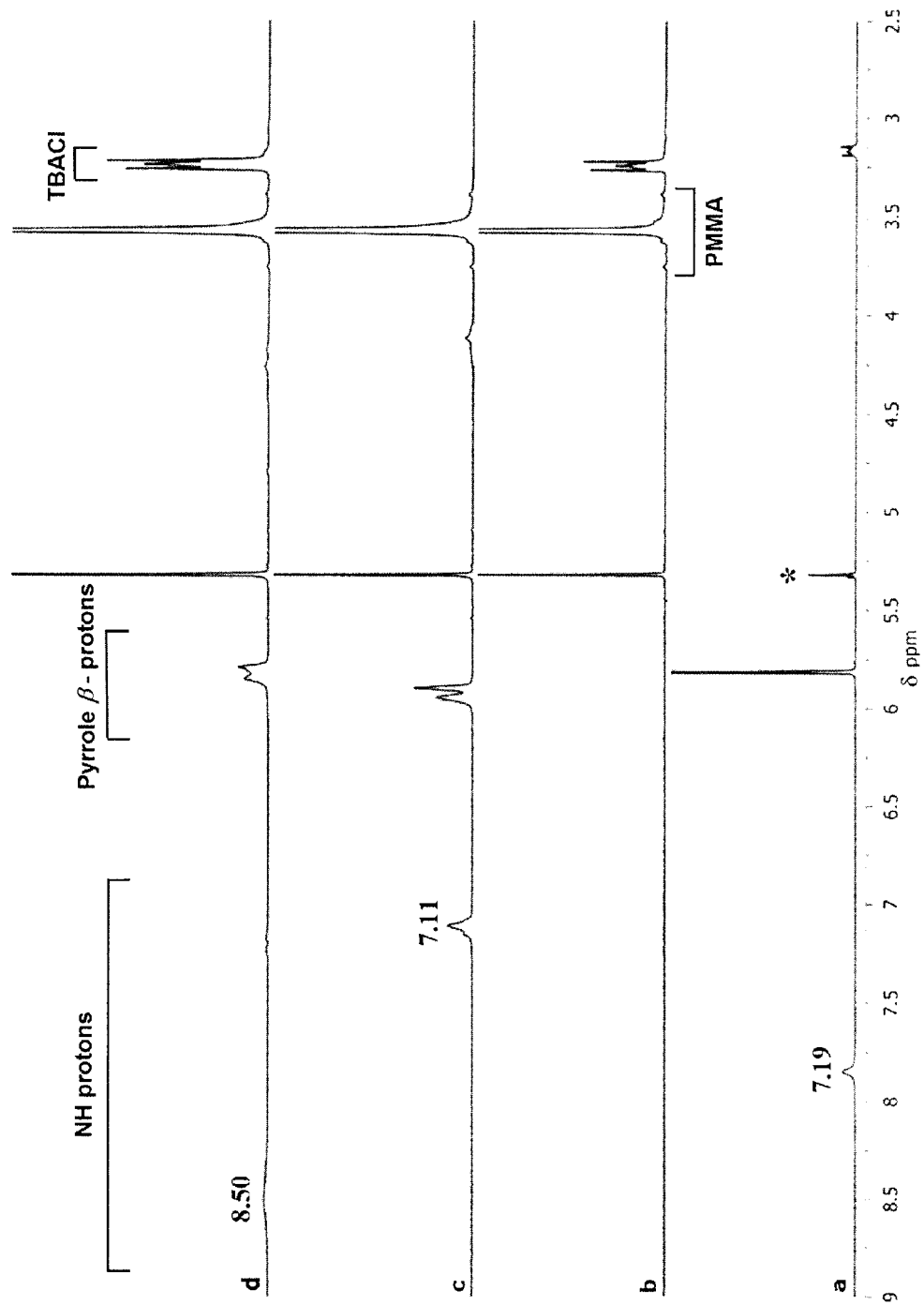
FIG. 2 shows overlaid $^1H$ NMR spectra of $CD_2Cl_2$ solutions of (a) a mixture of octamethylcalix[4]pyrrole (29 mM) and (b) PMMA (125 mM based on the repeat unit) after i) adding 0.5 mL of a $D_2O$ solution of TBACl (108 mM), ii) shaking the tube vigorously, and iii) allowing the phases to separate, (c) a calix[4]pyrrole functionalized co-polymer (effective concentration of the calix[4]pyrrole repeat unit=6.5 mM), and (d) a solution of the co-polymer after being subjected to the same treatment applied in the case of (a) and (b) (* indicates residual solvent).

The ability of the co-polymer to extract several other TBA$^+$ salts was also examined. While no extraction was seen in the case of aqueous solutions of tetrabutylammonium dihydrogen phosphate, upon addition of TBACl downfield shifts in the NH proton signals were seen to be greater than those observed with TBAF for analogous anion concentrations (see FIG. 2). Such results, which are consistent with an enhanced ability to extract chloride relative to fluoride or dihydrogen phosphate, run counter to the relative anion affinities seen in dichloromethane. However, they are in accord with what one would expect based on the so-called Hofmeister bias (see R. Custelcean and B. A. Moyer, *Eur. J. Inorg. Chem.* 2007, 1321-1340; F. Hofineister, *Arch. Exp. Pathol. Pharmakol.* 1888, 24, 247-260), namely that a more hydrophobic anion, such as chloride ($\Delta G_h = -340$ kJ mol$^{-1}$), is extracted more easily than a highly hydrophilic species, such as dihydrogen phosphate ($\Delta G_h = -465$ kJ mol$^{-1}$), or fluoride ($\Delta G_h = -465$ kJ mol$^{-1}$). See Table 1.1 of B. A. Moyer and P. V. Bonnensen, *Physical Factors in Anion Separations*, in Supramolecular Chemistry of Anions, A. Bianchi, K. Bowman-James, and E. García-España, Eds., Wiley-VCH, New York, 1997. Consistent with this rationale is the finding that both the control MMA homopolymer and calixpyrrole were able to extract TBACl under the aforementioned interfacial conditions, albeit with efficiencies of less than 35% relative to the co-polymer (as calculated from NMR integrations of the MMA methyl ester, β-pyrrolic, and TBA$^+$ signals, as appropriate). On the other hand, that efficient extraction of TBAF was only seen in the case of the co-polymer (and not the PMMA control or free calixpyrrole) underscores the notion that the calixpyrrole receptor appended to the PMMA backbone is playing a role in overcoming the Hofineister bias associated with this highly hydrophilic species.

Further support that the co-polymer could bind fluoride and chloride anions came from thermal analyses. Specifically, after independently exposing TBAF or TBACl to the co-polymer as described above, these samples as well as PMMA controls were subjected to thermogravimetric analysis. For the sample of the co-polymer exposed to TBAF, a 10% mass loss was observed upon heating to 230° C., a temperature just below the $T_d$ of the copolymer (262° C.). This compares well with the theoretical mass loss of 11.5% assuming the TBAF became completely volatilized over the aforementioned temperature range and was present in a 1:1 stoichiometry relative to each calix[4]pyrrole unit in the polymer chain. In contrast, the sample of the co-polymer exposed to TBACl exhibited a 19% mass loss (theoretical: 12.1%) upon heating to 230° C. Considering the relative extraction abilities of the co-polymer towards TBACl and TBAF (see above), the observed mass loss was considered reasonable. For comparison, the PMMA controls lost 2% of their masses prior to polymer decomposition (277° C.), which leads to the conclusion that only minimal amounts TBAF or TBACl were present in these samples after extraction.

Example 3

Preparation of Calix[4]pyrrole and benzo-15-crown-5 ether Functionalized PMMA Co-Polymers All solvents were dried before use according to standard literature procedures. Unless specifically indicated, all other chemicals and reagents used in this study were purchased from commercial sources and used as received. $^1$H, $^{13}$C and $^{19}$F NMR spectra used in the characterization of products and quantification of extracted KF were recorded on Varian Unity 300 or 400 MHz and Bruker 250 MHz AC-3000 spectrometers using a residual protio solvent as the reference. Low-resolution FAB and Cl mass spectra were obtained on a Finningan MAT TSQ 70 mass spectrometer (Finningan MAT; San Jose, Calif.). High resolution FAB and Cl mass spectra were obtained on a VG ZAB2-E mass spectrometer (Kevex/Fisons Instruments; San Carlos, Calif.). GPC analyses were performed using a Waters HPLC system consisting of HR-1, HR-3, and HR-5E Styragel® columns arranged in series, a 1515 pump, and a 2414 RI detector; reported molecular weights are relative to polystyrene standards in DMF (0.01 M LiBr) at 40° C. (column temperature) (Waters Corporation; Milford, Mass.). Thermogravimetric analyses were performed using a Mettler Toledo TGA/SDTA851e equipped with a TSO801RO sample automated loader (Mettler Toledo; Columbus, Ohio). A Varian SpectrAA-40 Atomic Absorption Spectrometer was used in flame emission mode with an acetylene/air (18:2) mixture to quantify the extracted potassium salts; the samples for these measurements were diluted with ethyl acetate prior to recording the emission intensities at 766.5 nm (Varian, Inc.; Palo Alto, Calif.). UV-vis analyses were performed with a Chebios Optimum-One UV-vis spectrophotometer (Chebios s.r.l.; Rome, Italy).

Synthesis

Three co-polymers were prepared based on the following formula:

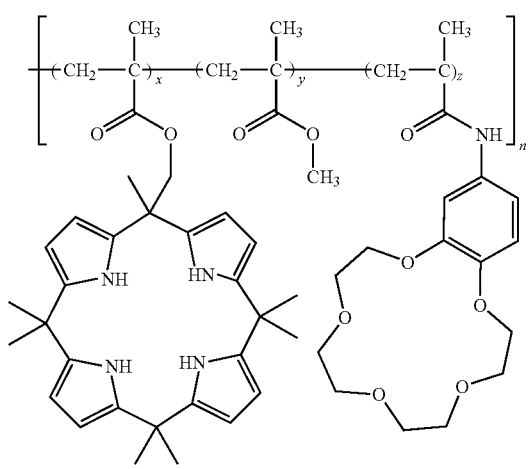

Specifically Copolymer I (x=1.0, y=14, z=0.8; $M_n$=57 kDa), Copolymer II (x=1.0, y=14, z=0; $M_n$=90 kDa), and Copolymer III (x=0, y=12, z=1.0; $M_n$=90 kDa) were prepared from MMA, calix[4]pyrrole, and a N-methylmethacrylamide benzo-15-crown-5 derivative using conventional free radical polymerization techniques as described above. (Copolymer II was prepared as above for Example 1.)

Copolymer I

Copolymer I was prepared by dissolving calix[4]pyrrole monomer, N-methylmethacrylamide benzo-15-crown-5 derivative monomer, and MMA in 1:1:10 ratio in THF (total conc.: approx. 0.3 M) followed by treatment with 1 mol % of azoisobutyronitrile (AIBN). After stirring at 70° C. for 17 h under an atmosphere of nitrogen, the resulting viscous solution was added dropwise to excess methanol. This caused precipitation of Copolymer I, which was subsequently isolated via filtration in 79% yield as a white solid. $^1$H NMR (500 MHz, CD$_2$Cl$_2$) δ: 0.82 and 0.89 (br singlets, 59.56H, PMMA CH$_3$), 1.51 (br s, 21H, calixpyrrole meso-CH$_3$), 1.82 (br m, 48.25H, PMMA CH$_2$), 3.57 (br s, 68H, PMMA OCH$_3$), 3.68 (br m, 7.5H, crown ether CH$_2$), 3.84 (br s, 3.75H, crown ether CH$_2$), 4.08 (br s, 6H, crown ether CH$_2$ and calixpyrrole meso-CH$_2$), 5.89 (b, 8H, pyrrole CH), 6.83-7.26 (6H, NH and crown ether aromatic protons). GPC: $M_n$: 50.2 kDa, PDI: 2.1.

Copolymer III

Using conditions analogous to those used to prepare Copolymer I, a 76% yield of Copolymer III was obtained as a yellow solid from a 1:10 mixture of N-methylmethacrylamide benzo-15-crown-5 derivative monomer and MMA. $^1$H NMR (500 MHz, CD$_2$Cl$_2$) δ: 0.81 (br s, 16.86H, polymer backbone CH3), 0.81 (br s, 10.30H, polymer backbone CH$_3$), 1.80 (br m, 19.12H, polymer backbone CH$_2$), 3.58 and 3.68 (s and s, 32.96H polymer backbone CH$_3$ and crown ether CH$_2$), 3.84 (br s, 2H, crown ether CH$_2$), 4.07 (br s, 2H, crown ether CH$_2$), 6.81-7.26 (3H, crown ether aromatic protons). GPC: M$_n$: 33.2 kDa, PDI: 2.1.

Example 4

Copolymer I can Extract Water Soluble Dyes with Chloride and Potassium Counterions Chloride Initial qualitative evidence that Copolymer I, which contains both calix[4]pyrrole and crown ether subunits, could extract chloride salts into organic media came from a visual test involving a water soluble dye that contains a chloride counteranion, specifically:

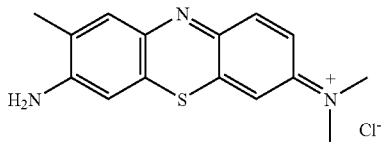

Figure 3:
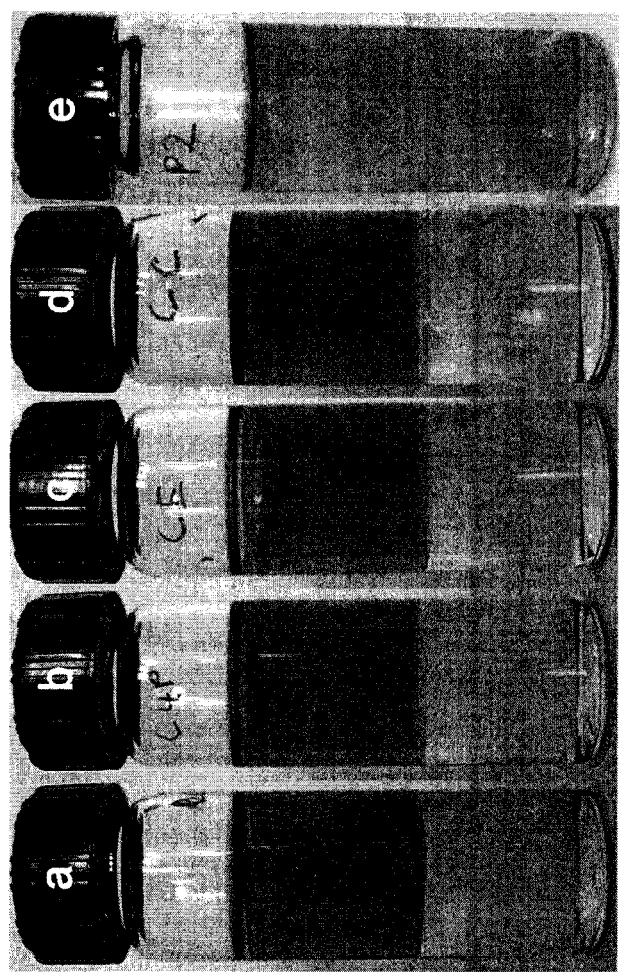
FIG. 3 shows aqueous solutions of a dye with a chloride anion (top layers) after treatment with: a) $CH_2Cl_2$ (bottom layer); b) a $CH_2Cl_2$ solution of octamethylcalix[4]pyrrole (bottom layer); c) a $CH_2Cl_2$ solution of benzo-15-crown-5 ether (bottom layer); d) a $CH_2Cl_2$ solution of the calix[4]pyrrole and the crown ether (bottom layer); and e) a $CH_2Cl_2$ solution of Copolymer I (bottom layer).
Figure 4:
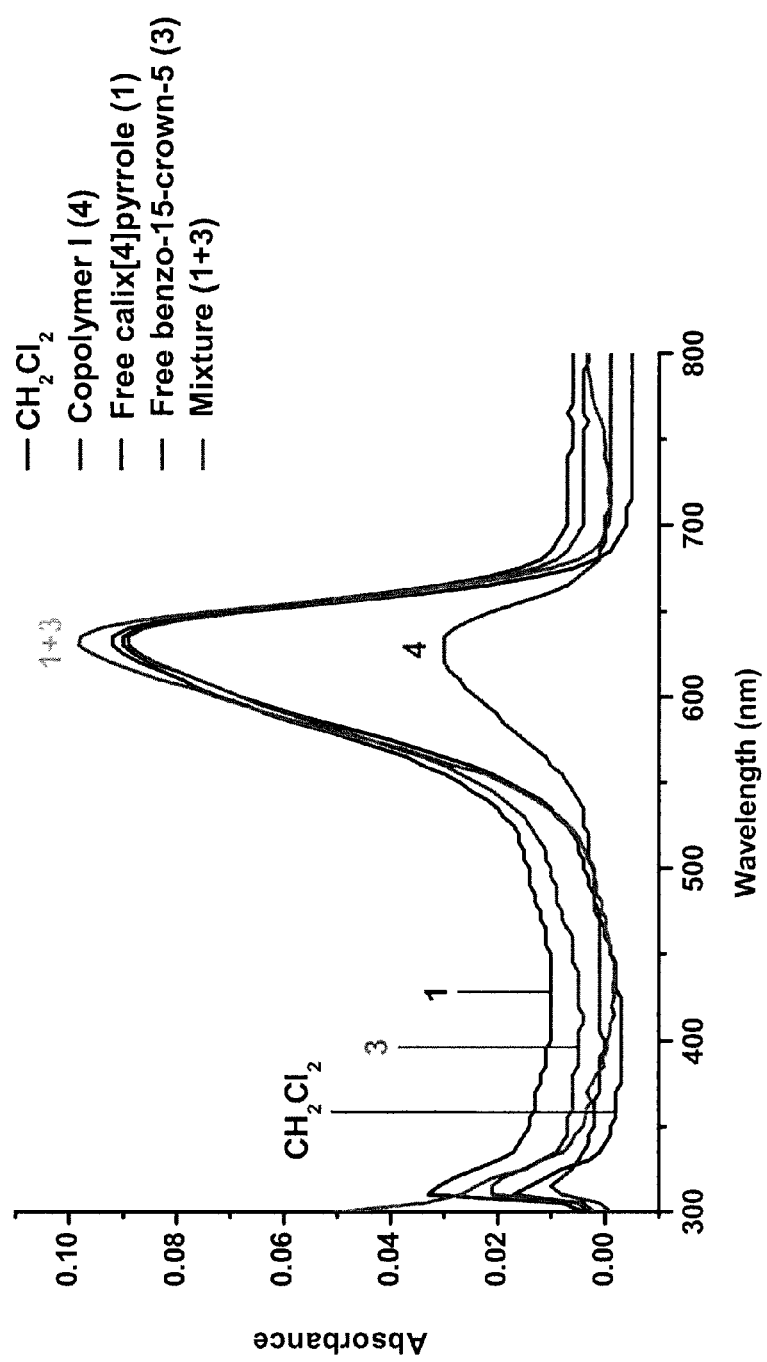
FIG. 4 shows UV-vis spectra of aqueous solutions of a dye with a chloride anion (initial concentration=25.5 μM) after exposing to an equal volume of a $CH_2Cl_2$ solution of Copolymer I (effective concentration of the calix[4]pyrrole and crown ether repeat units=1.56 and 1.22 mM), octamethylcalix[4]pyrrole (1.56 mM), benzo-15-crown-5 ether (1.22 mM), or a mixture of the calix[4]pyrrole and the crown ether (1.56 and 1.22 mM).

Extraction was performed by adding 3 mL of a organic solution to 3 mL of an aqueous solution containing the dye with vigorous shaking then allowing the organic and aqueous phases to separate. Treatment of an aqueous solution of the dye (25.5 µM) with a CH$_2$Cl$_2$ solution of Copolymer I (effective concentration of the calix[4]pyrrole and crown ether repeat units=1.56 and 1.22 mM, respectively) resulted in a colored organic (lower) phase (see FIG. 3e). As controls, solutions of the dyes were also exposed to a CH$_2$Cl$_2$ solution (see FIG. 3a), a CH$_2$Cl$_2$ solution of free calix[4]pyrrole (1.56 mM) (see FIG. 3b), a CH$_2$Cl$_2$ solution of free benzo-15-crown-5 (1.22 mM) (see FIG. 3c), and a mixture of free calix[4]pyrrole and free benzo-15-crown-5 in CH$_2$Cl$_2$ (1.56 and 1.22 mM, respectively) (see FIG. 3d), however no transfer of color was observed from the upper aqueous phase to the lower organic phase. These results were quantified using UV-vis spectroscopy (1 mL aliquots of the solutions were diluted to 10 mL with water then analyzed). As shown in FIG. 4, analysis of the water phases of these extraction experiments confirmed that Copolymer I was able to extract the dye into the organic phase more effectively (>54%) than free calix[4]pyrrole, free benzo-15-crown-5, or their mixture.

Potassium

Similar qualitative and quantitative results were observed when aqueous solutions of a water soluble dye that contains a potassium counteraction was examined. The dye had the following structure:

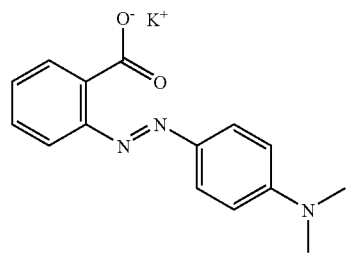

Figure 5:
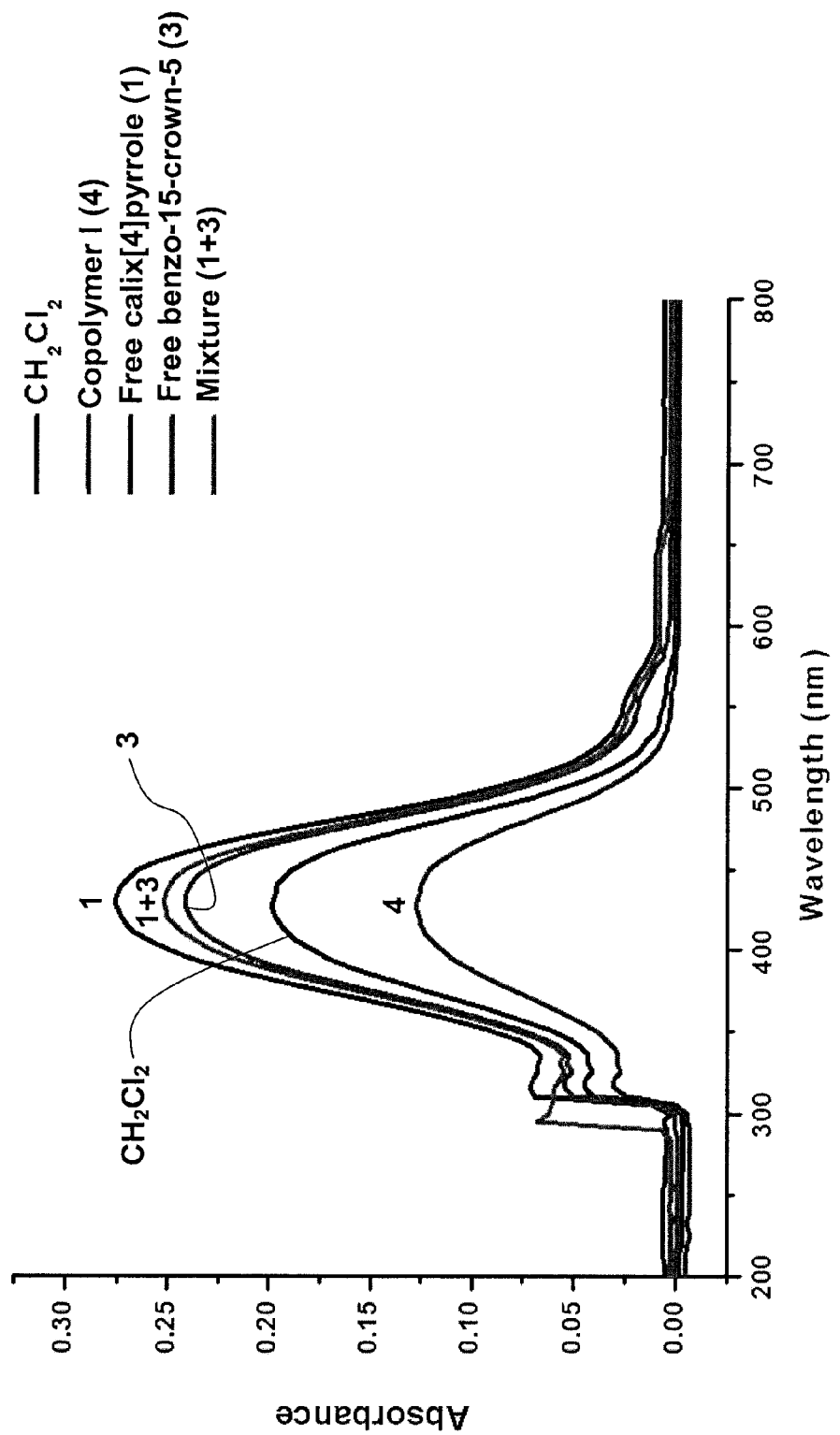
FIG. 5 shows UV-vis spectra of aqueous solutions of a dye with a potassium cation (initial concentration=216.86 after exposing to an equal volume of a $CH_2Cl_2$ solution of Copolymer I (effective concentration of the calix[4]pyrrole and crown ether repeat units=1.56 and 1.22 mM), octamethylcalix[4]pyrrole (1.56 mM), benzo-15-crown-5 ether (1.22 mM), or a mixture of the calix[4]pyrrole and the crown ether (1.56 and 1.22 mM).

In this case, Copolymer I proved more effective as an extractant (>30%) relative to free calix[4]pyrrole, free benzo-15-crown-5, or their mixtures (as used above) (see UV-vis spectroscopy results in FIG. 5).

Example 5

Copolymer I can Extract Potassium Fluoride

Figure 6:
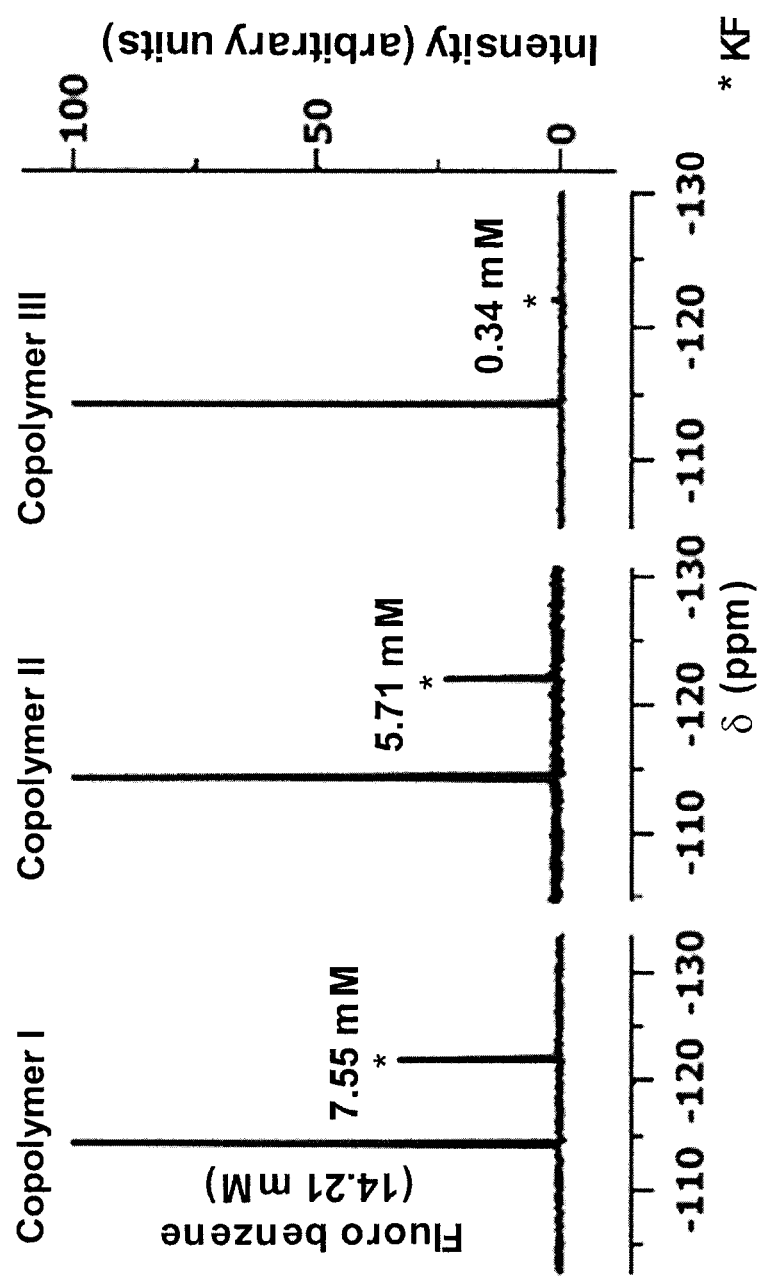
FIG. 6 shows $^{19}F$ NMR spectra of $CD_2Cl_2$ solutions of Copolymer I (effective [calix[4]pyrrole]=6.25 mM), Copolymer II ([calix[4]pyrrole]=6.50 mM), and Copolymer III (no calix[4]pyrrole) after adding $D_2O$ solutions of KF (3.4 M).

Whether Copolymer I could extract a salt consisting of two hard ions, namely potassium fluoride was examined using $^{19}$F NMR. In parallel, the extraction properties of Copolymer II and Copolymer III were examined to assess the relative importance of each individual ion recognition unit on the overall extraction properties of Copolymer I. To prepare the samples, a D$_2$O solution of KF (0.5 mL, 3.4 M) was added to a 0.75 mL sample of a CD$_2$Cl$_2$ solution of the individual polymer under investigation (i.e., Copolymer I, Copolymer II, or Copolymer III, respectively, as well as various controls). To each sample, 1 µL (14.21 mM) of fluorobenzene was added as an internal $^{19}$F NMR standard. After shaking the tubes vigorously, the phases were separated by subjecting them to centrifugation for 10 min. The CD$_2$Cl$_2$ layer obtained from each tube was then recorded using $^{19}$F NMR spectroscopy and the amount of KF was quantified via peak integration relative to the internal fluorobenzene standard. Following this procedure, the error in fluoride anion concentration measured in the extraction experiments described in the text was estimated to be less than 0.03 mM. As shown in FIG. 6, addition of a 3.4 M D$_2$O solution of KF to a CD$_2$Cl$_2$ solution of Copolymer I (effective concentration of the calix[4]pyrrole and crown ether repeat units=6.25 and 4.86 mM, respectively) resulted in the appearance of a signal at $\delta=-121.7$ ppm in the $^{19}$F NMR spectrum of the organic phase (the tubes were shaken vigorously, and then the phases were separated with the aid of centrifugation (10 min)). A similar signal, but of reduced intensity, was seen in the case of Copolymer II, whereas very little signal was observed in the case of Copolymer III.

To quantify the amount of fluorine present in the organic phases of the KF extraction experiments, fluorobenzene (final concentration: 14.21 mM) was added to each sample as an internal standard ($\delta=-114.3$ ppm). Based on comparative integrations (i.e., comparing total fluoride content in the CD$_2$Cl$_2$ layer relative to this standard), Copolymer I was found to be capable of extracting KF more efficiently (7.55±0.04 mM) then Copolymer II (5.71±0.03 mM) under conditions where the effective concentration of the calix[4]pyrrole repeat units in both polymers were essentially the same (6.25 mM versus 6.50 mM for Copolymer I and Copolymer II, respectively). In addition, both Copolymer I and Copolymer II were found to extract more fluoride into the organic phase than Copolymer III ([F]=0.34±0.03 mM in the CD$_2$Cl$_2$ layer), which that does not contain any calix[4]pyrrole subunits, as noted above. As control experiments, extractions were also performed in an analogous manner using free calix[4]pyrrole, free benzo-15-crown-5, MMA homopolymer, an equimolar mixture of free calix[4]pyrrole and free benzo-15-crown-5, and a calyx[4]pyrrole-benzo-15-crown-5 pseudo dimer, which was envisioned as a small molecule analogue of Copolymer I. No quantifiable fluorine signal was observed in the organic phase when any of these control systems were used as extractants.

Flame emission spectroscopy (FES) was used to confirm the co-extraction of potassium in the above experiments (see K. W. Jackson, S. J. Lu, Anal. Chem. 1998, 70, 363). A calibration curve was generated using a standard solution of potassium tetrakis(2-thienyl)borate (PTTB) in ethyl acetate/methylene chloride (9/1 v/v). The error in potassium concentrations measured following the extraction experiments is estimated to be less than 0.05 mM. The organic phase obtained after extracting KF with Copolymer I afforded an emission intensity (EI) of 0.401 (at 766.5 nm, i.e., the emission wavelength of the excited potassium ion produced by the flame source) after dilution with a known amount of ethyl acetate. By way of comparison, the organic phases produced EI values of 0.277 and 0.038, respectively when Copolymers II and III were used as extractants under otherwise identical conditions. Extracted potassium concentrations of 6.84, 4.73, and 0.65±0.05 mM were calculated for $CD_2Cl_2$ solutions of Copolymers I, II, and III (at effective crown ether concentrations of 5.60, 0.00, and 5.00 mM). These values agree with those obtained from the $^{19}F$ NMR data. A summary of the KF extraction data is presented in Table 1.

TABLE 1

Summary of KF extraction efficiencies.[a]

| Compound | calix:crown[c] | eff. (%) (total)[d,e] | eff. (%) (calix)[d,f] | eff. (%) (total)[e,g] | eff. (%) (crown)[g,h] |
|---|---|---|---|---|---|
| Copolymer I | 1.0:0.8 | 67 | 121 | 61 | 137 |
| Copolymer II | 1.0:0.0 | 88 | 88 | 73 | [i] |
| Copolymer III | 0.0:1.0 | 6 | [i] | 12 | 12 |
| Pseudo dimer[b] | 1.0:1.0 | 0 | 0 | 0 | 0 |

[a]Extraction efficiencies (eff.) are reported as the percent (%) of extractant populated with KF upon exposure to a saturated aqueous solution of KF.
[b]calix[4]pyrrole-benzo-15-crown-5 pseudo dimer
[c]Relative molar ratios of calixpyrrole (calix) to crown ether (crown) units in the extractant.
[d]Calculated from total fluoride extracted.
[e]Based on the total number of ion receptors (calixpyrrole plus crown ether) in the extractant.
[f]Based on the total number of calixpyrrole units in the extractant.
[g]Calculated from total potassium extracted.
[h]Based on the total number of crown ether units in the extractant.
[i]Not determined.

Example 6

Copolymer I can Extract Potassium Chloride

The ability of Copolymers I, II, and III to extract KCl from aqueous media was evaluated using conditions analogous to those employed for the KF studies described in Example 5. In this case, after exposing the polymers to 3.4 M solutions of KCl in $D_2O$, FES was again used to determine the relative amounts of potassium extracted. Copolymer I proved to be the most effective extractant, displaying an EI value of 0.761, which corresponded to a potassium concentration of 12.97±0.08 mM in the organic phase, with the exact quantification being based on the calibration described above. Copolymers II and III displayed relatively lower EI values, namely 0.507 and 0.081, respectively, values that corresponded to potassium concentrations of 8.64 and 1.38±0.08 mM, respectively. The higher overall extraction values for KCl compared to KF is consistent with the relative aqueous solvation energies ($\Delta G_h$) of chloride and fluoride anions ($\Delta G_h$=−340 kJ mol$^{-1}$ for Cl versus $\Delta G_h$=−465 kJ mol$^{-1}$ for F$^-$). Specifically, the more hydrophobic anion (Cl$^-$) was extracted more effectively than its more hydrophilic analogue (F$^-$).

Example 7

Copolymer I can Selectively Extract Potassium Ions

Whether potassium salts could be selectively extracted in the presence of their sodium analogues was examined. A 0.5 mL $H_2O$ solution of KCl (134.1 mM) and $NaNO_3$ (1.47 M) was treated with Copolymer I (in 0.75 mL $CH_2Cl_2$) and analyzed using FES (using the methods described above in Experiment 5). KCl and $NaNO_3$ were combined deliberately to form NaCl in situ. The EI of the signal corresponding to potassium (0.734) was over an order of magnitude greater than the signal corresponding to sodium (0.043). These data suggest that Copolymer I extracts potassium chloride much more effectively than it does sodium chloride. This finding, which is in accord with the relative hydration energies of K$^+$ and Na$^+$ ($\Delta G_h$=−295 kJ mol$^{-1}$ for K$^+$ and $\Delta G_h$=−365 kJ mol$^{-1}$ for Na$^+$), suggests that these materials may ultimately enable the selective separation of potassium halide salts from complex aqueous mixtures, e.g., in specialty medical applications.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents may be explicitly mentioned herein; however, all other combinations of steps, elements, components, and constituents are included, even though not explicitly stated.

What is claimed is:

1. A polymeric compound comprising the following calix [4]pyrrole monomeric unit:

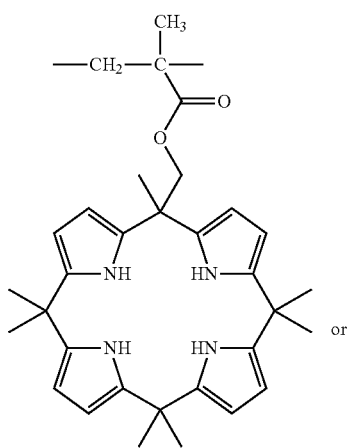

-continued

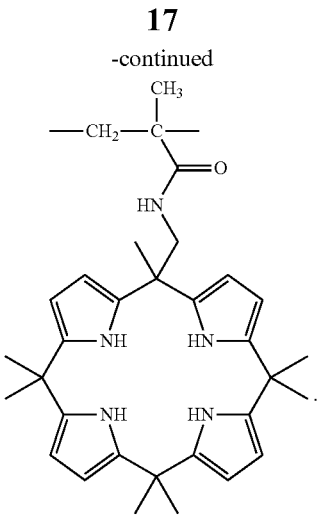

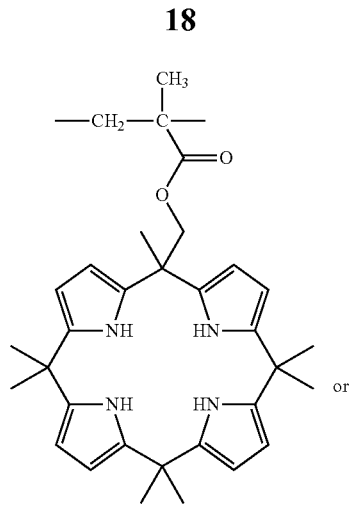 or

2. The polymeric compound of claim 1, further comprising the following methyl methacrylate monomeric unit:

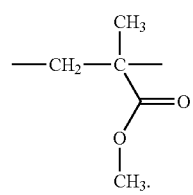

3. The polymeric compound of claim 2, further comprising the following benzo-15-crown-5 ether monomeric unit:

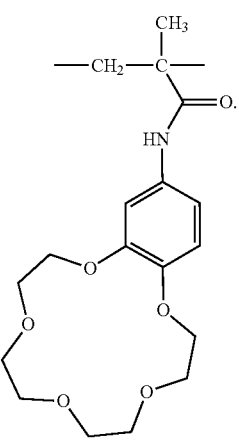 [SMILES: CCC(C)(C)C(=O)Nc1ccc2c(c1)OCCOCCOCCOCCO2]

4. The polymeric compound of claim 1, wherein the polymeric compound is further functionalized with a zwitterion-specific recognition element.

5. A method of removing an ionic species from a solution comprising adding a polymeric compound comprising the following calix[4]pyrrole monomeric unit:

to the ionic species in the solution.

6. The method of claim 5, wherein the ionic species is a cationic species.

7. The method of claim 5, wherein the ionic species is an anionic species.

8. The method of claim 5, wherein the ionic species is a zwitterionic species.

9. The method of claim 5, wherein the ionic species comprises a mixture of two or more ionic species selected from cations, anions, and zwitterions.

10. The method of claim 5, wherein the polymeric compound further comprises the following methyl methacrylate monomeric unit:

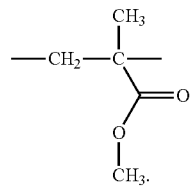

11. The method of claim 10, wherein the polymeric compound further comprises the following benzo-15-crown-5 ether monomeric unit:

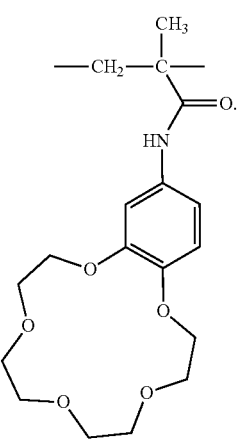 [SMILES: CCC(C)(C)C(=O)Nc1ccc2c(c1)OCCOCCOCCOCCO2]

12. The method of claim 5, wherein the polymeric compound is further functionalized with a zwitterion-specific recognition element.

13. A method of treating an ion imbalance in a subject comprising:
    selecting a subject with or suspected of having an elevated level of an ion; and
    administering to the subject a polymeric compound comprising the following calix[4]pyrrole monomeric unit:

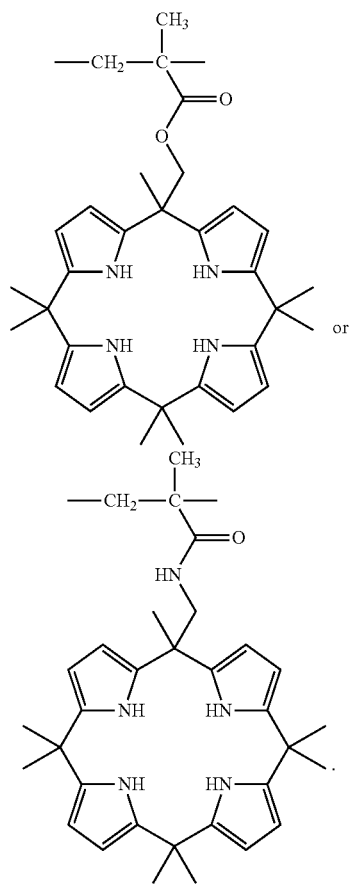

14. The method of claim 13, wherein the ion is a cation.
15. The method of claim 13, wherein the ion is an anion.
16. The method of claim 13, wherein the ion is a zwitterion.

17. The method of claim 13, wherein the ion comprises a mixture of two or more ionic species selected from cations, anions, and zwitterions.

18. The method of claim 13, wherein the polymeric compound further comprises the following methyl methacrylate monomeric unit:

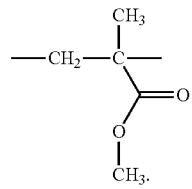

19. The method of claim 18, wherein the polymeric compound further comprises the following benzo-15-crown-5 ether monomeric unit:

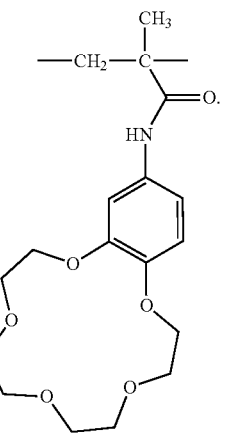

20. The method of claim 13, wherein the polymeric compound is further functionalized with a zwitterion-specific recognition element.

21. The polymeric compound of claim 1, wherein the polymeric compound is a homopolymer of one of the following calix[4]pyrrole monomeric units:

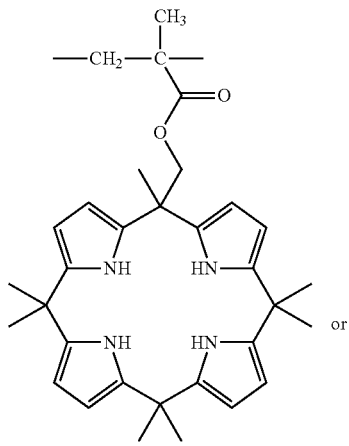

-continued
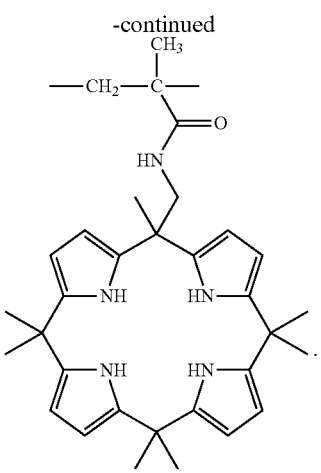
22. The method of claim 5, wherein the polymeric compound is a homopolymer of one of the following calix[4] pyrrole monomeric units:
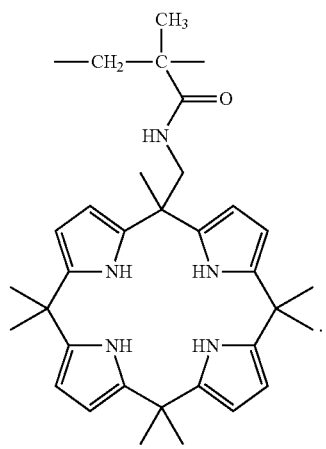
23. The method of claim 13, wherein the polymeric compound is a homopolymer of one of the following calix[4] pyrrole monomeric units:
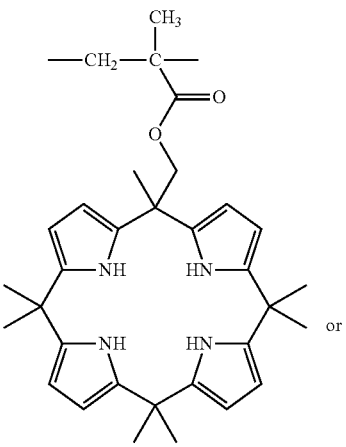
* * * * *

UNITED STATES PATENT AND TRADEMARK OFFICE
CERTIFICATE OF CORRECTION

PATENT NO. : 8,802,074 B2
APPLICATION NO. : 12/623943
DATED : August 12, 2014
INVENTOR(S) : Jonathan L. Sessler et al.

It is certified that error appears in the above-identified patent and that said Letters Patent is hereby corrected as shown below:

In the Specification

In column 1, lines 14-17, the statement regarding Federally sponsored research, which reads "This invention was made with government support from the National Institutes of Health Grant number GM-58907 and the National Science Foundation Grant number CHE-0645563. The government has certain rights in this invention."

should read --This invention was made with government support under Grant no. 0645563 awarded by the National Science Foundation; and Grant no. GM058907 awarded by the National Institutes of Health. The government has certain rights in the invention.--

Signed and Sealed this
Ninth Day of June, 2015

Michelle K. Lee
*Director of the United States Patent and Trademark Office*